US005962664A

United States Patent [19]
Friedhoff et al.

[11] Patent Number: 5,962,664

[45] Date of Patent: Oct. 5, 1999

[54] PSYCHOSIS PROTECTING NUCLEIC ACID, PEPTIDES, COMPOSITIONS AND METHOD OF USE

[76] Inventors: Arnold J. Friedhoff, 1382 Lexington Ave., New York, N.Y. 10128; Daryl A. Basham, 115-46 174th St., St. Albans, N.Y. 11434; Jeannette C. Miller, 50 E. 89th St., New York, N.Y. 10128

[21] Appl. No.: 08/602,716

[22] PCT Filed: May 13, 1994

[86] PCT No.: PCT/US94/05445

§ 371 Date: Feb. 23, 1996

§ 102(e) Date: Feb. 23, 1996

[87] PCT Pub. No.: WO94/26107

PCT Pub. Date: Nov. 24, 1994

Related U.S. Application Data

[63] Continuation-in-part of application No. 08/060,560, May 13, 1993, abandoned.

[51] Int. Cl.[6] .......................... C07H 21/04; C12N 15/63; C12N 15/85; C07K 14/00

[52] U.S. Cl. ..................... 536/23.1; 435/320.1; 435/325; 536/23.5; 536/24.31; 530/350

[58] Field of Search .................................... 435/325, 348, 435/69.1, 70.1, 70.3, 71.1, 71.2, 320.1; 536/23.1, 23.5, 24.3, 24.31, 24.33; 530/300, 324–328, 333, 412, 350

[56] References Cited

U.S. PATENT DOCUMENTS 4,552,865 11/1985 Itoh et al. .
5,089,397 2/1992 Kushner et al. .
5,098,888 3/1992 Vincent et al. .
5,149,786 9/1992 Ramirez et al. .
5,182,262 1/1993 Leto .

FOREIGN PATENT DOCUMENTS

92/16547 10/1992 WIPO .
93/00359 1/1993 WIPO .

OTHER PUBLICATIONS

Sambrook et al., *Molecular Cloning A Laboratory Manual*, 2nd ed., Cold Spring Harbor Laboratory Press, Plainview, N.Y., pp. 1.3–1.20 & 1.74–1.91, 1989.

Reeck et al., *Cell*, vol. 50, p. 667, 1987.

Saxe et al., *Mol. Cell. Bio.*, vol. 10, pp. 2367–2378, 1990.

Adams, M.D. et al, "Rapic cDNA sequencing (expressed sequence tags) from a directionally cloned human infant brain cDNA library", *Nature* Genetics vol. 4, pp. 373–380, Aug. 1993.

Perrett, C.W. et al., "Changes in brain gene expression in schizophrenic and depressed patients" Schizophrenia Research, vol. 6, No. 3, pp. 193–200 (1992) see abstract.

*Primary Examiner*—Paula K. Hutzell
*Assistant Examiner*—Stephen Gucker
*Attorney, Agent, or Firm*—Browdy and Neimark

[57] ABSTRACT

Psychosis protecting (PP) nucleic acids and encoded PP peptides and related proteins, and antibodies, anti-idiotype antibodies, and fragments thereto, for treatment, diagnosis and/or research related to the protection from psychosis such as schizophrenia or related disorders, or symptoms thereof, and expression products, compositions and methods therefor, including treatment of schizophrenia and related disorders, as well as transgenic non-human mammals epxressing PP peptide or related protein encoding nucleic acids.

27 Claims, 3 Drawing Sheets

SEQUENCE LISTING

```
(1) GENERAL INFORMATION:

   (iii) NUMBER OF SEQUENCES: 12


(2) INFORMATION FOR SEQ ID NO:1:

     (i) SEQUENCE CHARACTERISTICS:
          (A) LENGTH: 26 base pairs
          (B) TYPE: nucleic acid
          (C) STRANDEDNESS: single
          (D) TOPOLOGY: linear

    (ii) MOLECULE TYPE: cDNA

        (xi) SEQUENCE DESCRIPTION: SEQ ID NO:1:

TTTTTTTTTT TTTTTTCCCC GGGCTA                                            26


(2) INFORMATION FOR SEQ ID NO:2:

     (i) SEQUENCE CHARACTERISTICS:
          (A) LENGTH: 22 base pairs
          (B) TYPE: nucleic acid
          (C) STRANDEDNESS: single
          (D) TOPOLOGY: linear

    (ii) MOLECULE TYPE: cDNA

        (xi) SEQUENCE DESCRIPTION: SEQ ID NO:2:

ATCGAAATTC CCCCCCCCCC CC                                                22


(2) INFORMATION FOR SEQ ID NO:3:

     (i) SEQUENCE CHARACTERISTICS:
          (A) LENGTH: 371 base pairs
          (B) TYPE: nucleic acid
          (C) STRANDEDNESS: single
          (D) TOPOLOGY: linear

    (ii) MOLECULE TYPE: cDNA

        (xi) SEQUENCE DESCRIPTION: SEQ ID NO:3:
```

TTTTCAGCAG TTGGCCTTTG TTGAGAAAAT GTGTGACTTT GCCCAAGCCC AGTAACTTGG 60

AGCCTTGAAT TTGAGATGCT GGAAAGGGAG TCCTTCCTCC TTTCTGCAGT GTTGTCCCTA 120

GTTTACCAAA GTCCATTTTG AATGTACCAT CCCCAGCCCA ACTCCAGCCT ACAGATAGTG 180

CCAGACCGCC AGTAGGTGAG TAGCACTGTC TTCCTGGTCC GGACCTAGTG GCTTTGCTGT 240

TAGGACCTTA TCACTAGAGA TGGCCTGGAT TTAGAGACGA ACCATTAGCT GTTGCCATAG 300

CTGTTGCCAT ATGATTACGT GGCCTTGGGT TTCGCAATAA TTTATTTGGG TTCACTAAAT 360

TTTAAATTTC T 371

(2) INFORMATION FOR SEQ ID NO:4:

(i) SEQUENCE CHARACTERISTICS:
(A) LENGTH: 206 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:4:

TTCGTATGGA CTCGGAATAA AGTAAGTGTT TTCAGCCTGG CTGGATGTAT GTTGCAAAAT 60

GGCCTCGATT CACCCAGGGC AATAAACAGT GGTATTGATA ACCCAAAACA ATAGTAATTG 120

AAAATAATTT GTTTTAAAAG TATATGCTTT TCTTTTGATA CTCAAGTGTT TCATATTAGA 180

GGTAAATGAG AAAATATAGA TGAACC 206

(2) INFORMATION FOR SEQ ID NO:5:

(i) SEQUENCE CHARACTERISTICS:
(A) LENGTH: 110 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:5:

TTTGGAAGAT TTATTAATTG ATTAAGGACT AGGAGGTCCA GCTAAAATGC AATTGGATTT 60

ATTAAGGTAC TTAAATCCAG ATTTAAGGTA TGAAATCAAG AATGGCGAAC 110

(2) INFORMATION FOR SEQ ID NO:6:

(i) SEQUENCE CHARACTERISTICS:
(A) LENGTH: 359 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:6:

TCCAAGAACA GTTTTGGGCC AAACAGACGA ACAGCCAGTT GGTTTTCTAT ACCAACTGTG 60

TGATTTATTA GAGCTGTCAC ATGCTATCAT GAACTGCGCT GTACGAAGTC AACTCAGTGA 120

TGATGTGAGG TATCACTACT AGTTGGTTGG TTGGTTACAT ATCTTAAATA TGTAGACAAC 180

TTACCAACTG GAATGTTCAG CTAGCTAATA TCTCAATTAG AATCCATCTC ACTAGGAATG 240

GGCAAACACT TGTGTTCTAA AGTTACTTGA AAGTAGTTTA TACTGCCAAC TTGATATATA 300

TCATGCTATA GTTTGAACAT TTTGTGTACT TCCAAAATTC ACATTAAAAT CTAATCCAC 359

(2) INFORMATION FOR SEQ ID NO:7:

(i) SEQUENCE CHARACTERISTICS:
(A) LENGTH: 201 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:7:

```
TTTAGTTAGC TGGGCCTACA GGCATGCACC ACCACCATTG GCTAAGTTTT GTATTTTCAG     60

TAGAGACAGG GTTCACCATG TTGGCCAGGC TGCTCTTGAA CTCCTGACCT CAAGTGATCC    120

ACCTACCTCC GCCTCCGAAA AGTGCTAGGA TTACAGGCCT GAGCCACTGT GCCTGGCCTG    180

ATAAAGCACA TTTAAAGATC T                                              201
```

(2) INFORMATION FOR SEQ ID NO:8:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:8:

```
ATTGCACTCC ATCCAGCCTG GGCAACAAGA GAGAAACTCC ATCTC                     45
```

(2) INFORMATION FOR SEQ ID NO:9:

(i) SEQUENCE CHARACTERISTICS:
(A) LENGTH: 174 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:9:

```
TGTCTCTAGT AAAAATACAA AAATTGGCCG AGCGTGAAGG CTGGCGCCTC TAATCCCAGC     60

TTCTTGGGAA GCTGAGGGAA GCTGAGGCAC AAGAATTTGC TTGAGCCCAC GAGTGGTTGA    120

ATGCCAGGAC CTGTCCACTG CACTCCAGCC TGGGCGACAG AACGACACTG TCTC          174
```

(2) INFORMATION FOR SEQ ID NO:10:

(i) SEQUENCE CHARACTERISTICS:
(A) LENGTH: 212 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:10:

```
GTCTGGAGTT CAAAACCATC CTGGCATTTA TGGTGAAACC CTGTCTCTAC TAAAAATACA     60

AAATAGACAG GTGTGGGTGT CACGCCTGTA GTCCCAGCTA CTCGGAAGGC TGAGGCAGGA    120

GAATCGCTTG AACCTGGGAG GCAGAGGTTG CATTGAGGCA AGATCGCACC ACTGTACTCC    180

AGCCAGGGTG ACAGAGCGGG ACTCTGTCAT TT                                  212
```

(2) INFORMATION FOR SEQ ID NO:11:

(i) SEQUENCE CHARACTERISTICS:
(A) LENGTH: 247 base pairs
(B) TYPE: nucleic acid
(C) STRANDEDNESS: single -continued

```
        (D) TOPOLOGY: linear

    (ii) MOLECULE TYPE: cDNA

        (xi) SEQUENCE DESCRIPTION: SEQ ID NO:11:

ATGTTATCCC TTGAATGTAG TGTGTAACAG AGAGAGATGT TTCTTTCTTT CTTTGATTAT     60

CTGAGAAGCT AGGCAGGTGA AAGAACTTTC TTGTCCTCCA TTCAGAAATA ATTTACAGGC    120

AGTTACTTCT AAATATGCAT GCCTGGGCCA AATGTGGTGG CTCACACCTG TAATCCCAAC    180

CCTGGGAAGC TGAGGCAGGA GGATTGCTTG CAACCAGCCT GGGTAGACAT AGTGAAACCT    240

GTCTCTC                                                              247

(2) INFORMATION FOR SEQ ID NO:12:

     (i) SEQUENCE CHARACTERISTICS:
          (A) LENGTH: 32 base pairs
          (B) TYPE: nucleic acid
          (C) STRANDEDNESS: single
          (D) TOPOLOGY: linear

    (ii) MOLECULE TYPE: cDNA

        (xi) SEQUENCE DESCRIPTION: SEQ ID NO:12:

AGCCTGGGCG ACAGAGAGCC AAACGCCGTC TG                                   32
```

PSYCHOSIS PROTECTING NUCLEIC ACID, PEPTIDES, COMPOSITIONS AND METHOD OF USE

CROSS REFERENCE TO RELATED APPLICATIONS

The present application is a 35 USC 371 application of PCT/US94/05445, filed May 13, 1994, and a continuation-in-part of application No. 08/060,560, filed May 13, 1993, now abandoned.

This invention was made with Government support under MH 35976 and MH 08618 awarded by the National Institute of Mental Health. The Government thus has certain rights in the invention.

BACKGROUND OF THE INVENTION

1. Field of the Invention

The present invention relates to the field of molecular biology and medicine, and more particularly to psychosis protecting (PP) nucleic acids and peptides involved in protection from psychoses and related disorders, as well as expression products, compositions thereof, and methods therefor, including detection, amplification, isolation and expression of such PP nucleic acids and PP peptides, as well as diagnostic and therapeutic methods using such PP peptides and their encoding PP nucleic acid.

2. Background of the Related Art

Psychoses, such as schizophrenia can be differentiated into two basic categories; those which are amenable to treatment, by means of conventional antipsychotic drugs, and those which are resistant to treatment, the latter usually being spoken of as "chronic" or "negative symptom" schizophrenia. Preclinical conditions of psychoses are also prevalent and could be subject to treatment if the degree of severity could be diagnosed in a standardized manner. These categories can, to some degree, be correlated with the relative balance of positive and negative symptomatology. The designation "negative (Bleulerian) symptomatology", although long known, has in recent years been used more routinely.

Treatment of psychoses and schizophrenia. Treatment of schizophrenia and other psychoses is commonly provided using the antipsychotics termed neuroleptic agents. Neuroleptic agents, regardless of their chemical structures, are pharmacologically active upon the dopamine receptor system, as dopamine antagonists. Many of these compounds, particularly the phenothiazines, also have significant activity on other neurotransmitter systems, in particular various serotonin subtypes, particularly the 5-HT-2, and on muscarinic receptors, alpha-adrenoceptors, or histamine H-1 or H-2 receptors. The clinical use of neuroleptics has provided a means for treating patients suffering from psychotic disorders, including schizophrenia. Short-term use of neuroleptics is indicated in several types of exacerbations of schizophrenia. Continuous long-term use of neuroleptics is indicated, e.g., in primary indications involving schizophrenia as well as questionable indications such as chronic characterological disorders with schizoid, "borderline," or neurotic characteristics. See, e.g., Baldessarini, *Chemotherapy in Psychiatry*, Revised and Enlarged Edition, Harvard University Press, Cambridge, Mass., (1985), the contents of which are entirely incorporated herein by reference.

Neuroleptics and Their Side Effects. Neuroleptics are also referred to as neuroplegics, psychoplegics, psycholeptics, antipsychotics and major tranquilizers, but are sometimes distinguished from non-neuroleptic psychotropics. Neuroleptics have also been characterized as agents that produce sedative or tranquilizing effects, and which also produce motor side effects, such as catalepsy or extrapyramidal symptomatology. Nonlimiting representative examples of neuroleptics include phenothiazine derivatives (e.g., chlorpromazine); thioxanthine derivatives (e.g., thiothixene); butyrophenone derivatives (e.g., haloperidol); dihydroindolone (e.g., molindone); dibenzoxazepine derivatives (e.g., loxapine); and "atypical" neuroleptics (e.g., sulpiride, remoxipride pimozide and clozapine). See Berstein *Clinical Pharmacology* Littleton, Mass.:PSG Publishing (1978); Usdin et al *Clinical Pharmacology in Psychiatry* New York:Elsevier North-Holland (1981); and Baldessarini, supra, (1985); which references are herein entirely incorporated by reference.

The long term use of all known anti-psychotics, including neuroleptics, has resulted in serious side effects, as set forth in Table I, such as persistent and poorly reversible motoric dysfunctions (e.g., tardive dyskinesia) in a significant number of patients. For example, classical neuroleptic agents, as exemplified by the butyrophenones and phenothiazines, can, upon long-term administration, produce severe motoric symptomatology, termed tardive dyskinesia. These motor movements are uncontrollable and can range from relatively trivial manifestations to total debilitation. Tardive dyskinesia is usually reversible upon discontinuation of the chronic neuroleptic, if the drug is discontinued soon after symptoms of tardive dyskinesia appear. Otherwise symptoms may persist. Pharmacological intervention for treatment of tardive dyskinesia is only moderately successful. Such motor abnormalities are known to occur in as high as 10% of the patients who are maintained on these drugs for several years; the incidence is much greater in certain groups, such as middle-aged females.

The following Table I presents these and additional neurological side effects of neuroleptic anti-psychotic drugs.

TABLE I

Neurological Side Effects of Neuroleptic-Antipsychotic Drugs

| Reaction | Features | Period of maximum risk | Proposed mechanism | Treatment |
|---|---|---|---|---|
| Acute dystonia | Spasm of muscles of tongue, face, neck, back; may mimic seizures; not hysterical | 1–5 days | Dopamine excess? Acetylcholine excess? | Antiparkinsonism agents are diagnostic and curative (i.m. or i.v., then p.o.) |
| Parkinsonism | Bradykinesia, rigidity, | 5–30 days | Dopamine blockade | Antiparkinsonism agents |

TABLE I-continued

Neurological Side Effects of Neuroleptic-Antipsychotic Drugs

| Reaction | Features | Period of maximum risk | Proposed mechanism | Treatment |
|---|---|---|---|---|
| | variable tremor, mask-facies, shuffling gait | (rarely persists) | | (p.o); dopamine agonists risky? |
| Akathisia | Motor restlessness; patient may experience anxiety or agitation | 5–60 days (commonly persists) | Unknown | Reduce dose or change drug low doses of propranolol;[a] antiparkinsonism agents or or benzodiazepines may help |
| Tardive dykinesia spontaneous | Oral-facial dyskinesia; choreo-athetosis; sometimes irreversible, rarely progressive | 6–24 months (worse on withdrawal) | Dopamine excess? | Prevention best; treatment unsatisfactory; slow remission |
| "Rabbit" syndrome | Perioral tremor (late parkinsonism variant?); usually reversible | Months or years | Unknown | Antiparkinsonism agents; reduce dose of neuroleptic |
| Malignant syndrome | Catatonia, stupor, fever, unstable pulse and blood pressure; myoglobinema; can be fatal | Weeks | Unknown | Stop neuroleptic; antiparkinsonism agents usually fail; bromocriptine often helps; denatrolene variable; general supportive care crucial |

In addition, clozapine, although apparently capable of producing less motor side effects, can cause irreversible, potentially fatal agranulocytosis in a minority of patients administered the drug. Such serious side effects limit the use of clozapine to patients who are resistant to treatment with other neuroleptics.

These side effects are especially prevalent in geriatric populations, and adequate pharmacological treatment of these debilitating motoric dysfunctions is not currently available. This problem has been generally associated with long-term, clinical administration of these agents, including their use in the long term treatment of schizophrenia. There is thus a great need for alternative treatments for schizophrenia, including chronic schizophrenia, without toxic side effects of known agents used for such treatment, or whose long-term administration will not produce such toxic side effects.

Treatments proposed for schizophrenia. Anti-psychotic drugs, such as neuroleptics have been found to generally affect neuroreceptors, such as dopamine and serotonin receptors. Many of these receptors have been recently cloned and sequenced, such as the serotonin 5-HT1 and 5-HT2 (see, e.g., Leonard, *Int. Clin. Psychopharmacol.*, 7(1):13–21 (1992)) and dopamine receptors: D5 (Sunahara et al., *Nature*, 350:614–619 (1991)); D4 (Van Tol et al., *Nature*, 350:610–614 (1991)); D1 (Zhou et al., *Nature*, 347:76–80 (1990); Dearry et al., *Nature*, 347:72–76 (1990)); and rat D2 (Tourtellotte et al., *Neurochem. Res.*, 12:565–571 (1987); Bunzow et al, *Nature*, 33:783–787; Miller et al, *Biochem. Biophys. Res. Com.*, 166:109–112)).

Currently anti-psychotic agents (neuroleptics) are used for the treatment of schizophrenia and all other psychoses. Proposed treatments involve the use of compositions containing peptides and proteins which may act as ligands for receptors or portions of receptors as well as other neural active peptides and analogs thereof. Examples of such compositions include neurotensin peptide analogs (WO 93/00359, Du Pont Merck Pharmaceutical Co. (1993)), tachykinin agonists (WO 92/22569, Fujisawa Pharmaceutical Co., LTD. (1992); EP 482 539, Fujisawa Pharmaceutical Co., LTD. (1992)), galanin agonists (WO 92/20709, Astra AB (1992)), neurokinin receptor and fragments (WO 92/16547, Children's Medical Center (1992); dopamine receptor agonist/antagonist peptides (WO 91/04271, BASF AG, (1991)), thyrotropin releasing hormone analogs (U.S. Pat. No. 5,098,888, Vincent et al (1992)), enkephalin like peptides (WO 90/00564, Research Corp. Techn., Inc. (1990); U.S. Pat. Nos. 4,684,620 (1987) and 4,518,711 (1985), Hruby et al; EP 050 828, Merck, Inc. (1984)), calmodulin binding peptides (U.S. Pat. No. 5,182,262, Hruby (1993)), cerulein peptides (U.S. Pat. No. 4,552,865, Fujino et al (1985)), and dopamine releasing protein (U.S Pat. No. 5,149,786, Marcus et al. (1992)).

Citation of documents herein is not intended as an admission that any of the documents cited herein is pertinent prior art, or an admission that the cited documents are considered material to the patentability of any of the claims of the present application. All statements as to the date or representation as to the contents of these documents is based on the information available to the applicant and does not constitute any admission as to the correctness of the dates or contents of these documents.

SUMMARY OF THE INVENTION

It is an object of the present invention to overcome one or more deficiencies of the related art.

It is another object of the present invention to provide a psychosis protecting gene and expression products thereof, such as psychosis protecting (PP) peptides or psychosis protecting nucleic acids that are expressed in normal people, but not expressed in patients diagnosed with clinical schizophrenia or other psychoses.

It is a further object of the present invention to provide methods for detecting the relative lack of expression of a psychosis protecting gene in a mammal, having a maximum range of expression that correlates with at least one clinical symptom associated with a psychotic disorder. These symptoms of various psychoses include thought disorders, affectual blunting, delusions, hallucinations, anhedonic cognitive impairment.

It is yet a further object of the present invention to provide a means for diagnosing impending psychosis in individuals at risk for schizophrenia or other psychoses who do not express genes or DNA comprising a sequence corresponding to a PP peptide or related peptide or protein.

It is yet another object of the present invention to use a portion of a nucleic acid sequence corresponding to a DNA sequence according to SEQ ID NO:3 as a probe to obtain and/or sequence a full length gene as expressed in lymphocytes or other accessible tissues and in brain tissue from psychotic and normal individuals or animals.

Another object of the present invention is to use the gene fragment as described in SEQ ID NO:3 to identify the DNA that corresponds to a PP peptide or protein and to identify the full length DNA that represents an extension of the present gene fragment.

It is also an object of the present invention to make an animal model of psychosis or animals vulnerable to psychosis by inhibiting the expression of PP peptide related proteins in rats, mice or other non-human species. In one aspect, a transgenic experimental animal is provided which has been transformed by the gene carrying the nucleic acid sequences inhibiting the expression of PP peptide related proteins so as to obtain an animal model exhibiting psychotic symptoms and the corresponding neurophysiology. One example of such an inhibiting nucleic acid sequence encoding an antisense nucleic acid which is complementary to the DNA sequence of (SEQ ID NO:3).

The present invention is also directed to a transgenic laboratory animal as a model of a psychotic disorder which is produced by inserting a PP peptide related protein inhibiting nucleic acid of this invention into a mouse or other suitable laboratory animal so that the animal displays psychotic symptoms corresponding to a known psychotic disorder. Such an animal model enables testing on non-humans of treatment and diagnostic methods for psychotic disorders, such as schizophrenia, schizoaffective disorders, paranoid disorders, and some mood disorders.

It is also an object of the present invention to enable genetic counselors to provide information about the risk of schizophrenia or other psychoses by determining whether the protective gene described herein is actively expressed in an individual at risk for psychosis.

It is also an object to provide methods for treating psychoses by providing expression or expression products of a psychosis protecting gene as therapeutic compounds, compositions and methods.

It is another object of the present invention to provide monoclonal antibodies, anti-idiotype antibodies, or fragments thereof, which specifically bind an epitope of a psychosis protecting peptide.

It is yet another object of the present invention to provide PP peptides, antibodies, anti-idiotype antibodies, compositions and methods that can be used in therapeutic and/or diagnostic applications for psychosis, due to their expected biological properties.

A further object of the present invention is to provide synthetic, isolated or recombinant peptides which are designed to inhibit or mimic various PPs or fragments thereof, which are effective for the treatment or diagnosis of symptoms relating to schizophrenia or other psychoses.

It is another object of the present invention to provide non-naturally occurring synthetic, isolated and/or recombinant PP peptides which are fragments and/or muteins of polypeptides encoded by the gene, a fragment of which is the DNA sequence of (SEQ ID NO:3), or at least one of SEQ ID NOS:4–12, which encoded PP peptides are expected to have therapeutic effects in psychotic patients and which are useful for providing diagnostic, therapeutic or research compounds, compositions and methods of use.

In a preferred embodiment, the peptide is (a) chemically synthesized and/or (b) obtained from a recombinant host cell or organism which expresses a recombinant nucleic acid encoding a PP peptide, as defined herein, and/or may be provided as a therapeutic or diagnostic nucleic acid.

In another aspect of the present invention, a PP composition is provided, comprising at least one PP peptide, or a pharmaceutically acceptable ester, ether, sulfate, carbonate, malate, glucuronide or salt thereof, the PP composition optionally further comprising a pharmaceutically acceptable carrier and/or diluent.

In still another aspect of the present invention, a method is provided for treating a subject suffering from symptoms associated with schizophrenia or any other psychotic disorder.

In a preferred embodiment, the PP peptide corresponds to an active portion of a protein encoded by the genes, fragments of which are the nucleic acid sequences of SEQ ID NO:3, or SEQ ID NOs:4–12, wherein the method comprises administering an effective psychosis treating modulating amount of a PP peptide of the present invention. In another preferred embodiment, the disease state is a psychiatric disorder related to schizophrenia or schizo-affective disorder, or any other psychotic disorder, see American Psychiatric Association, *Revised Manual of Diagnostic and Statistical Criteria for Psychiatric Disorders* (DSM-III-R), American Psychiatric Assoc. Press, Washington, D.C. (1989), hereinafter "Criteria for Psychiatric Disorders" which is entirely incorporated herein by reference.

In another preferred embodiment, the PP composition is administered as a pharmaceutical composition to provide a PP peptide in an amount ranging from about 0.01 μg to 100 mg/kg, and also preferably, about 10 μg to 10 mg/kg. In another preferred embodiment, the administeration is by oral, intravenous, intramuscular, parenteral or topical administration, including mucosal administration to the nasal mucosa or the oral mucosa, by aerosol, nebulizer or drop administration as non-limiting examples.

Other objects of the invention will be apparent to skilled practitioners from the following detailed description and examples relating to the present invention.

BRIEF DESCRIPTION OF THE DRAWINGS

(FIG. 3B) control showing absence of hybridization.

DETAILED DESCRIPTION OF THE INVENTION

Figure 1:
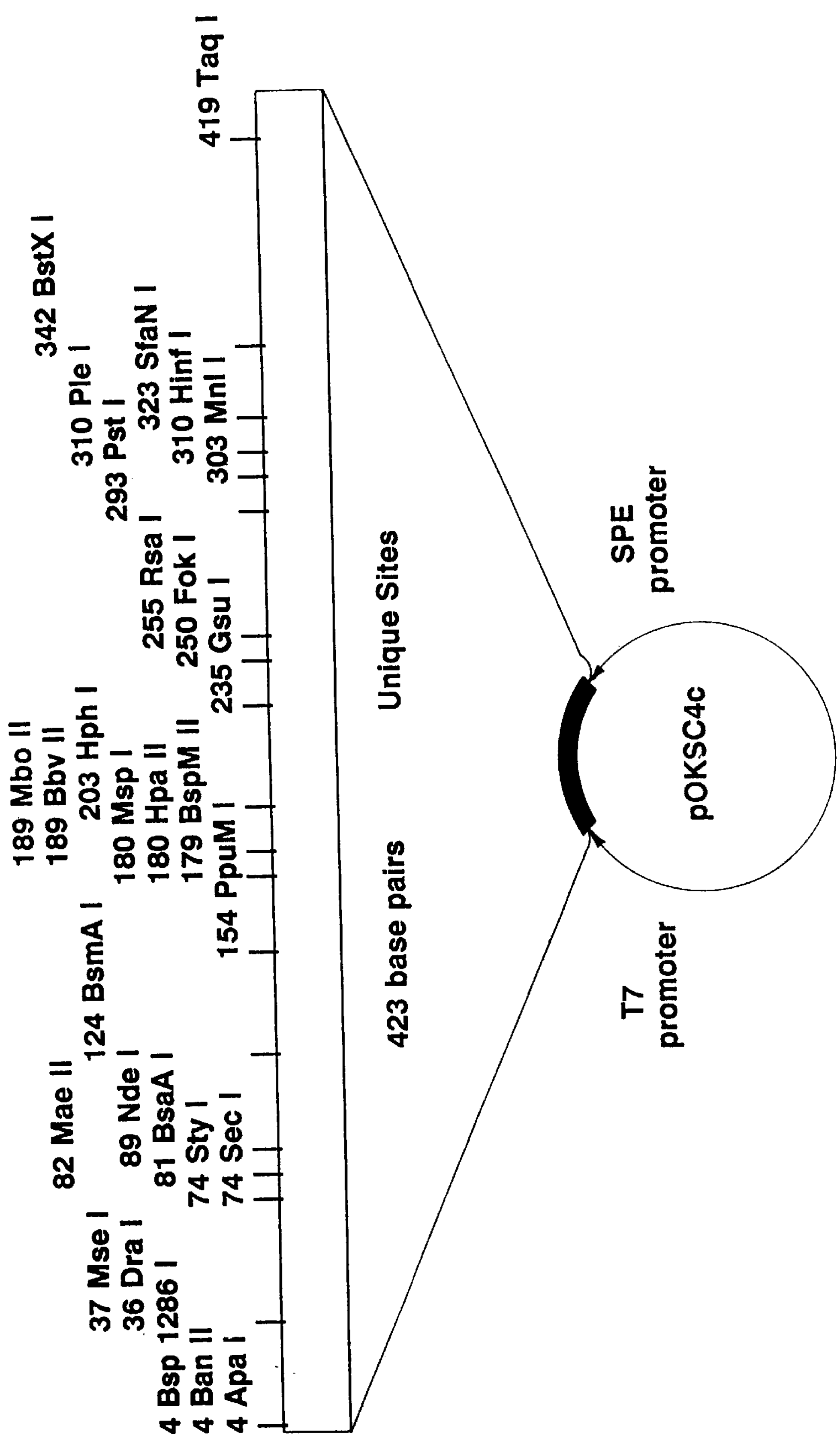
FIG. 1 is a diagram depicting a vector pOKSC4c.

Based on the discovery that normal monozygotic twins express a protein which is not expressed in corresponding schizophrenic monozygotic twins, and which psychotic preventing (PP) peptide related protein is only found to be expressed in areas of the cerebral cortex known to include neurotransmission involved in psychotic disorders, the present invention relates to PP peptides corresponding to functional domains of the normally expressed PP related protein. Such PP peptides are thus expected to be used to mimic naturally occurring, PP peptide related proteins, which are expected to have a protective and/or therapeutic effect on individuals suffering from symptoms relating to psychoses, such as schizophrenia or schizo-affective disorders or other psychoses (see, e.g., "Criteria for Psychiatric Disorders", supra).

The basis of the present invention was discovered in studies of schizophrenia involving monozygotic twins where one twin has symptoms of the disease and the other twin is normal, which thus provides a "control" for the other twin. Estimates of concordance rates for schizophrenia in monozygotic twins vary, but are in the fifty percent range. Inasmuch as both twins presumably have identical genes (verified by DNA fingerprinting) and immunological markers, the clinical manifestations of the illness might be determined by other factors as well. If schizophrenia is of multifactorial etiology (i.e., having multiple gene and environmental components), the application of quantitative genetic analysis may be inappropriate in the elucidation of the molecular etiology of the illness. One alternative approach is to study gene expression in affected individuals and controls.

Thus the present invention involved the subtraction cloning of cDNA from mRNA of such monozygotic twins to determine if a psychosis protecting gene was expressed in normal twins and not in psychotic twins. The discovery of such a PP peptide encoding gene, and confirmation of expression in the cortex where neurotransmission effects associated with psychotic disorders has been determined, has provided a means to clone and express such PP related proteins and related or functionally similar PP peptides, as well as antibodies thereto, which are expected to be useful in the treatment, diagnosis and/or research involving psychotic disorders in humans and animals.

Accordingly, a "psychosis protecting peptide" or "PP peptide" of the present invention includes peptides having a "PP amino acid sequence" which can be obtained initially by using the sequence presented in SEQ ID NO:3, or SEQ ID NOs:4–12, as a basis for designing polynucleotide probes to clone, sequence and express or synthesize PP related proteins and peptides occurring in normal individuals, and to a substantially lesser degree in individuals with psychotic disorders, such as polypeptides encoded in part by at least one gene, a fragment of which is at least one nucleic acid sequence of SEQ ID NOs:3–12.

PP peptide nucleic acid probe detection of PP peptide epitope containing peptides or proteins. PP peptide nucleic acid probes may be used to detect RNA or DNA encoding PP peptide related or homologous proteins as a means to diagnose or prediagnose psychosis or related disorders, such as schizophrenia. Such nucleic acid probes may thus be used to quantitatively or qualitatively detect an RNA or DNA encoding a protein or peptide corresponding at least in part to a PP peptide in a sample or to detect the presence of such nucleic acids in biological fluids or cells which express such nucleic acid, in vitro, in situ, or in vivo, based on the teaching and guidance presented herein, without undue experimentation. The lack of, or presence of low concentrations of, nucleic acid encoding PP peptide related peptides and/or proteins is expected to correlate with psychoses and related disorders, such as schizophrenia.

Nucleic acid probe assays capable of detecting the presence of such a nucleic acid molecule, or proteins encoded therefrom, in a sample are well known in the prediction and diagnosis of disease. Nucleic acid detection assays can be predicated on any characteristic of the nucleic acid molecule, such as its size, sequence, susceptibility to digestion by restriction endonucleases, etc. Such a labeled, detectable probe can be used by known procedures for screening a genomic or cDNA library of a cell having a nucleic acid encoding a PP peptide related protein or peptide or as a basis for synthesizing PCR or other nucleic amplification probes for amplifying a cDNA generated from an isolated RNA encoding a target nucleic acid or amino acid sequence, as described herein.

A detectably labeled oligonucleotide probe of this sort can be a fragment of an oligonucleotide that is complementary to a polynucleotide encoding a PP peptide or fragment thereof. Alternatively, a synthetic oligonucleotide can be used as a target probe which is preferably at least about 10 nucleotide in length (such as 10, 15, 16, 17, 18, 19, 20, 21, 22, 23, 24, 25, 26, 27, 28, 29, 30, 35, 40, 45, 50, 60, 70, 80, 90, 100, or 100–423 or more, or any combination or range therein, in increments of 1 nucleotide), such that the target probe is specific for the desired nucleic acid sequence to be detected, amplified or expressed. Preferably the nucleotide probe corresponds to at least a portion of a nucleic acid sequence presented in SEQ ID NO:3.

Nucleic acids, or protein encoded thereby, to be detected by a method of the present invention, may be contained in samples isolated from any tissue sample of an animal subject or patient, such as blood, lymph, saliva, urine, CNS, amniotic fluid, skin, hair, feces, or any other tissue, and analyzed by hybridization to labeled probes. Such probes preferably hybridize to PP peptide-encoding nucleotide under high stringency conditions or medium stringency conditions, depending on the presence or possible presence of other non-target nucleic acids which also bind the probes specific for the target nucleic acids. For probe design, hybridization, and stringency conditions, see, e.g., Ausubel supra, sections 6.3 and 6.4, and Sambrook et al, supra.

A wide variety of such labels have been used for labeling detectable probes, which can be used for labeling nucleic acid containing probes, as follows: (1) Kourilsky et al. (U.S. Pat. No. 4,581,333), e.g., describe the use of enzyme labels to increase sensitivity in a detection assay; (2) radioisotopic labels are disclosed, e.g., by Falkow et al. (U.S. Pat. No. 4,358,535), and by Berninger (U.S. Pat. No. 4,446,237); (3) fluorescent labels of probes can be used (e.g., Albarella et al., EP 144914); (4) chemical labels of probes may be used (e.g., Sheldon III et al., U.S. Pat. No. 4,582,789, Albarella et al., U.S. Pat. No. 4,563,417); (5) modified bases in the probes may be used (e.g., Miyoshi et al., EP 119448); (6) a restriction enzyme sensitive label for differential restriction endonuclease digestion may be used (Saiki et al., *Biotechnology* 3:1008–1012, 1985), (7) an allele specific label using allele specific oligonucleotide probes may be used Saiki et al, *Nature* 324:163–166 (1986), Conner et al., *Proc. Nat'l Acad. Sci. USA*, 80:278 (1983), Holbeck and Nepom, *Immunogenetics* 24:251–258 (1986), Nepom et al, U.S. Pat. Nos. 5,039,606 and 4,971,902, and Whiteley et al, U.S. Pat. No. 4,833,750; (8) a ligase mediated label for ligase mediated gene detection (LMGD) using oligonucleotide ligation assays may also be used (Landegren, et al., *Science* 241: 1077–1080, 1988), and (9) a fluorescence energy transfer label for use in fluorescence resonance energy transfer (FRET), as disclosed, e.g., by Wolfe et al., *Proc. Nat. Acad. Sci. USA* 85: 8790–94 (1988)as non-limiting examples. See also, e.g., Ausubel et al, eds., supra; Sambrook, supra; Harlow, supra; and Coligan et al., supra, For related technologies and methods. See also, e.g., Ausubel, supra, at §§9.5.2 (selectable markers), §9.8 (RNA analysis), §§10.6-8 (detection of proteins), §§11.1-1.2 (immunoassays) and §§11.3.16 (preparation and use of monoclonal, polyclonal and antipeptide antibodies for protein detection). The above references are all entirely incorporated herein by reference.

Accordingly, detection of a nucleic acid encoding a PP peptide related protein or peptide can be provided according to the present invention, based on the teaching and guidance presented herein, without undue experimentation.

PP peptides of the present invention can include fragments and/or mutein peptides encoded by the genes, fragments of which are the nucleic acid sequences of SEQ ID NO:3; FIG. 1 (SEQ ID NO: 1) or at least one of SEQ ID NOs: 4–12, or amino acids encoded thereby, biological activity which modulates one or more symptoms associated with schizophrenia or schizo-affective disorders, such as delusions, hallucinations (particularly arbitrary), thought disorder and emotional blunting, which activity is measurable in vitro, in vivo or in situ, using known testing as screening assays. In the context of the present invention, "anti-psychotic biological activities" refers to having a detectable or measurable improved effect on at least one psychosis associated symptom, such as improved behavior, thought process, speech, thought content, improved perceptual abnormalities, affect, cognitive functions, and the like, as determined by known psychiatric evaluation techniques. See,., e.g., *Merck Manual*, supra, Chs. 133–136 and 140–143; and *Criteria for Psychiatric Disorders*, supra, which are entirely incorporated by reference herein.

Alternatively or additionally, screening may be carried out using the gene fragment as at least a 10 nucleotide sequence appearing in SEQ ID NO:3 or at least one of SEQ ID NOs:4–12) as a probe in Northern analysis or for dot blot or slot blot or other techniques for detecting specific RNA or DNA sequences, e.g., as substantially corresponding to at least one of SEQ ID NOs:3–12. Other methods for detecting the PP could also be used such as immunocytochemistry. Tissue sources of RNA could be lymphocytes or other accessible tissues, or any tissue capable of expressing a PP peptide or PP nucleic acid.

PP peptides of the present invention can be synthesized or recombinantly produced, or optionally purified, to provide commercially useful amounts of PP peptides for use in therapeutic, diagnostic or research applications, according to known method steps, see, e.g., Ausubel et al, eds. *Current Protocols in Molecular Biology*, Greene Publishing Associates and Wiley Interscience, N.Y., N.Y. (1987, 1993); Harlow and Lane, Antibodies: *A Laboratory Manual*, Cold Spring Harbor Press (1988); Sambrook et al, *Molecular Cloning, A Laboratory Manual*, 2nd edition, Vols. 1–3, Cold Spring Harbor Press, (1989); Coligan et al., eds., *Current Protocols in Immunology*, Greene Publishing Associates and Wiley Interscience, New York, N.Y., (1992, 1993), which references are herein entirely incorporated by reference.

Additionally, PP peptides according to the present invention can be used to generate polyclonal and/or monoclonal antibodies, anti-idiotype antibodies thereto, or fragments thereof, which may used for diagnostic and/or therapeutic applications, according to known method steps, see, e.g., Harlow, supra, which is herein entirely incorporated by reference.

PP peptides or anti-idiotype antibodies (or fragments thereof) to PP peptides are expected to be useful to quantitatively or qualitatively modulate or prevent the development and/or symptoms associated with psychoses and related disorders, such that administration of PP peptides and/or anti-idiotype antibodies (or fragments thereof) may be used for research or therapeutic applications of the present invention.

Anti-PP antibodies (or fragments thereof) to PP peptides are also expected to be useful to quantitatively or qualitatively modulate or prevent the development and/or symptoms associated with psychoses and related disorders, such that administration of anti-PP peptide antibodies (or fragments thereof) may be used for diagnostic or research applications of the present invention.

Such PP peptides, (including PP fragments, substitution derivatives and anti-idiotype antibody fragments) of the present invention may be used to treat symptoms of, and provide treatment for, pathologies related to psychose and related disorders. $D_2$ receptor-related psychotic disorders, including schizophrenia, now treated with neuroleptics, are non-limiting examples thereof.

The use of synthetic or recombinant PP peptides of the present invention can be preferable to the use of known drugs for schizophrenia and related disorders, e.g., which bind G-protein coupled receptors, such as neuroleptics that bind or inhibit the biological effect of binding to neuroreceptors as a non-limiting example. Such peptides are expected to have significantly less side effects than presently used drugs presently used for treating schizophrenia and related disorders, including neuroleptics, as they would structurally mimic naturally occurring PP peptides and/or modulate abnormal ligand binding. Thus, PP peptides are expected to have reduced side effects attributable to known foreign compound drugs, with less immunogenicity, and reduced potential for motoric side effects (e.g., extrapyramidal symptoms and/or tardive dyskinesia).

The present invention is also related to the production, by chemical synthesis or recombinant DNA technology, of PP peptides, preferably as small as possible while still retaining sufficient biological activity for protecting or treating the effect on patients having symptoms related to schizophrenia or other psychoses.

PP peptides of the present invention may include fragments of 5–10 to 50–150 amino acid fragments, or mutein sequences of PP peptides, including, e.g., homologs thereof having a homology of at least 80% with at least one PP peptide. See, e.g., Probst et al *DNA and Cell Biology* 11:1–20 (1992), which is entirely incorporated herein by reference.

Also preferred are PP peptides corresponding to proteins whose encoding nucleic acid gene hybridizes to polynucleotide probes corresponding to SEQ ID NO:3, wherein the PP amino acid sequence is 10 to 1000 amino acids in length, such as 10, 15, 20, 30, 40, 50, 60, 70, 80, 90, 100, 110, 120, 130, 140, 150, 160, 170, 180, 190, 200, 300, 400, 500, 600, 700, 800, 900 or 1000 amino acids, or any value or range therein.

An amino acid sequence of, or nucleic acid sequence encoding, a PP peptide of the present invention is said to "substantially correspond" to another amino acid or nucleic acid sequence, respectively, if the sequence of amino acids or nucleic acid in both molecules provides PP peptides having biological activity that is substantially similar in amino acid sequence of a PP peptide, such that only one to a few amino acids differ in amino acid sequence. Additionally or alternatively, such "substantially corresponding" sequences of PP peptides include conservative amino acid or nucleotide substitutions, or degenerate nucleotide codon substitutions wherein individual amino acid or nucleotide substitutions are well known in the art.

Accordingly, PP peptides of the present invention, or nucleic acid encoding therefor, include a finite set of substantially corresponding sequences as substitution peptides or polynucleotides which can be routinely obtained by one of ordinary skill in the art, without undue experimentation, based on the teachings and guidance presented herein. For a detailed description of protein chemistry and structure, see Schulz, G. E. et al., *Principles of Protein Structure*, Springer-Verlag, New York, 1978, and Creighton, T. E., *Proteins: Structure and Molecular Properties*, W.H. Freeman & Co., San Francisco, 1983, which are hereby incorporated by reference. For a presentation of nucleotide sequence substitutions, such as codon preferences, see Ausubel et al, supra, at §§ A.1.1–A.1.24, and Sambrook et al, supra, at Appendices C and D.

Conservative substitutions of a PP peptide of the present invention includes a variant wherein at least one amino acid residue in the PP peptide has been conservatively replaced by a different amino acid. Such substitutions preferably are made in accordance with the following list as presented in Table II, which substitutions may be determined by routine experimentation to provide modified structural and functional properties of a synthesized PP peptide molecule, while maintaining the psychosis treating or protecting biological activity.

TABLE II

| Original Residue | Exemplary Substitution |
|---|---|
| Ala | Gly;Ser |
| Arg | Lys |
| Asn | Gln;His |
| Asp | Glu |
| Cys | Ser |
| Gln | Asn |
| Glu | Asp |
| Gly | Ala;Pro |
| His | Asn;Gln |
| Ile | Leu;Val |
| Leu | Ile;Val |
| Lys | Arg;Gln;Glu |
| Met | Leu;Tyr;Ile |
| Phe | Met;Leu;Tyr |
| Ser | Thr |
| Thr | Ser |
| Trp | Tyr |
| Tyr | Trp;Phe |
| Val | Ile;Leu |

Alternatively, another group of substitutions of PP peptides of the present invention are those in which at least one amino acid residue in the protein molecule has been removed and a different residue inserted in its place according to the following Table III. The types of substitutions which may be made in the protein or peptide molecule of the present invention may be based on analysis of the frequencies of amino acid changes between a homologous protein of different species, such as those presented in Table 1–2 of Schulz et al., supra, and FIGS. 3–9 of Creighton, supra. Based on such an analysis, alternative conservative substitutions are defined herein as exchanges within one of the following five groups:

TABLE III

1. Small aliphatic, nonpolar or slightly polar residues: Ala, Ser, Thr (Pro, Gly);

2. Polar, negatively charged residues and their amides: Asp, Asn, Glu, Gln;

3. Polar, positively charged residues: His, Arg, Lys;

4. Large aliphatic, nonpolar residues: Met, Leu, Ile, Val (Cys); and

5. Large aromatic residues: Phe, Tyr, Trp.

Conservative amino acid substitutions according to the present invention, e.g., as presented above, are known in the art and would be expected to maintain biological and structural properties of a PP peptide after amino acid substitution. Most deletions and insertions, and substitutions according to the present invention are those which do not produce radical changes in the characteristics of the protein or peptide molecule. "Characteristics" is defined in a non-inclusive manner to define both changes in secondary structure, e.g. $\alpha$-helix or $\beta$-sheet, as well as changes in physiological activity, e.g. in receptor binding assays.

However, when the exact effect of the substitution, deletion, or insertion is to be confirmed one skilled in the art will appreciate that the effect of the substitution or substitutions will be evaluated by routine screening assays, either immunoassays or bioassays to confirm biological activity. For example, a substituted PP peptide typically is made by site-specific mutagenesis of a PP peptide encoding nucleic acid, expression of the mutant nucleic acid in recombinant cell culture, and, optionally, purification from the cell culture, for example, by immunoaffinity chromatography using a specific antibody on a chemically derivatized column or immobilized membranes or hollow fibers (to absorb the mutant by binding to at least one epitope).

A preferred use of this invention is the production, by chemical or recombinant DNA technology, of PP peptides, preferably as small as possible while still retaining schizophrenia or related disorder treating or preventing biological activity.

Antibodies, Anti-Idiotype Antibodies and Fragments Thereof for PP Peptides of the Present Invention, and Proteins and Peptides Related Thereto. This invention is also directed to antibodies ("Abs") or fragments thereof which bind at least one epitope specific for a PP peptide of the present invention. The present invention is also directed to methods using such an antibody or fragment to detect the presence of, or measure the quantity or concentration of, a protein or polypeptide sharing at least one epitope with a PP peptide, the protein or polypeptide being present in a cell, a cell or tissue extract, a biological fluid, an extract thereof, a solution, or sample, in vitro, in situ, or in vivo. Such methods provide a means to determine the extent, susceptibility or degree of psychosis or related disorders.

The term "anti-PP peptide antibody," or "anti-PP peptide Ab", is meant to encompass any antibody or fragment which specifically binds to any PP peptide epitope, including polyclonal antibodies, monoclonal antibodies (mAbs), chimeric antibodies, anti-idiotypic (anti-Id) antibodies to antibodies specific for PP peptides of the present invention, as well as fragments, consensus polypeptides or chemical derivatives thereof (as presented herein for PP peptides). Such anti-PP peptide Abs may be produced by any known method steps, including hybridoma, recombinant or synthetic production techniques. An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids, lipids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies which may be evoked by other antigens.

Polyclonal antibodies are heterogeneous populations of antibody molecules derived from the sera of animals immunized with an antigen. A monoclonal antibody contains a substantially homogeneous population of antibodies specific to antigens, which population contains substantially similar epitope binding sites.

Anti-PP peptide antibodies may be obtained by any method steps known to those skilled in the art. See, for example Kohler and Milstein, *Nature* 256:495–497 (1975); U.S. Pat. No. 4,376,110; Ausubel et al, eds., supra; Sambrook, supra; Harlow, supra; and Coligan et al., supra, the contents of which references are incorporated entirely herein by reference. Such antibodies may be of any immunoglobulin class including IgG, IgM, IgE, IgA, GILD and any subclass thereof. A hybridoma producing a mAb of the present invention may be cultivated in vitro, in situ or in vivo.

Chimeric antibodies are molecules of which different portions are derived from different animal species, such as those having variable region derived from a murine mAb and a human immunoglobulin constant region, which are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Cabilly et al, *Proc. Natl. Acad. Sci. USA* 81:3273–3277 (1984); Morrison et al., *Proc. Natl. Acad. Sci. USA* 81:6851–6855 (1984); Boulianne et al., *Nature* 312:643–646 (1984); Cabilly et al., European Patent Application 125023 (published Nov. 14, 1984); Neuberger et al., *Nature* 314:268–270 (1985); Taniguchi et al., European Patent Application 171496 (published Feb. 19, 1985); Morrison et al., European Patent Application 173494 (published Mar. 5, 1986); Neuberger et al., PCT Application WO 86/01533, (published Mar. 13, 1986); Kudo et al., European Patent Application 184187 (published Jun. 11, 1986); Morrison et al., European Patent Application 173494 (published Mar. 5, 1986); Sahagan et al., *J. Immunol.* 137:1066–1074 (1986); Robinson et al., International Patent Publication No. PCT/US86/02269 (published May 7, 1987); Liu et al., *Proc. Natl. Acad. Sci. USA* 84:3439–3443 (1987); Sun et al., *Proc. Natl. Acad. Sci. USA* 84:214–218 (1987); Better et al., *Science* 240:1041–1043 (1988); and Harlow and Lane, supra. These references are incorporated entirely herein by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference. The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity. Accordingly, mAbs generated against a PP peptide of the present invention may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a immunogenic carrier such as keyhole limpet hemocyanin (KLH) or cationized bovine serum albumin and used to immunize additional BALB/c mice. Sera from these mice will contain anti-anti-Id antibodies that have the binding properties of the original mAb specific for a PP peptide epitope. The anti-Id mAbs thus have their own idiotypic epitopes, or "idiotopes" structurally similar to the epitope being evaluated.

The term "antibody" is also meant to include both intact molecules as well as fragments thereof, such as, for example, Fab and $F(ab')_2$, which are capable of binding antigen. Fab and $F(ab')_2$ fragments lack the Fc fragment of intact antibody, clear more rapidly from the circulation, and may have less non-specific tissue binding than an intact antibody (Wahl et al., *J. Nucl. Med.* 24:316–325 (1983)). It will be appreciated that Fab and $F(ab')_2$ and other fragments of the antibodies useful in the present invention may be used for the detection and quantitation of a PP peptide according to the methods disclosed herein for intact antibody molecules. Such fragments are typically produced by proteolytic cleavage, using enzymes such as papain (to produce Fab fragments) or pepsin (to produce $F(ab')_2$ fragments). See, e.g., Harlow, supra, Coligan, supra, Ausubel, supra. Additionally, synthetic or recombinant antibody fragments may be used which bind epitopes of PP peptides or related proteins.

Epitopes recognized by antibodies, and fragments and regions thereof, of the present invention may include 5 or more amino acids of a PP peptide related protein provided according to the present invention using probes corresponding to, or complementary to a 10–421 base sequence of SEQ ID NO:3, which a topographical epitope of a PP peptide or related protein is recognized by, and specifically binds a anti-PP peptide antibody, fragments, and variable regions thereof.

The techniques to raise antibodies of the present invention to small peptide sequences that recognize and bind to those sequences in the free or conjugated form or when presented as a native sequence in the context of a large protein are well known in the art. Such antibodies include murine, murine human and human-human antibodies produced by hybridoma or recombinant techniques known in the art. See, Ausubel, supra, Harlow, supra, and Coligan, supra.

The identification of these peptide sequences recognized by mAbs of the present invention provides the information necessary to generate additional monoclonal antibodies with binding characteristics and therapeutic utility that parallel the embodiments of this application.

A PP-peptide specific murine, human or chimeric mAb of the present invention may be produced in large quantities by injecting hybridoma or transfectoma cells secreting the antibody into the peritoneal cavity of mice and, after appropriate time, harvesting the ascites fluid which contains a high titer of the mAb, and isolating the mAb therefrom. For such in vivo production of the mAb with a non-murine hybridoma (e.g., rat or human), hybridoma cells are preferably grown in irradiated or athymic nude mice.

Cell fusions for hybridoma formation of cells producing anti-PP peptide antibodies of the present invention may be accomplished by standard procedures well known to those skilled in the field of immunology (Kohler and Milstein, *Nature* 256:495–497 (1975) and U.S. Pat. No. 4,376,110; Hartlow, E. et al., supra; Campbell, A., "Monoclonal Antibody Technology," In: *Laboratory Techniques in Biochemistry and Molecular Biology*, Volume 13 (Burdon, R., et al., eds.), Elsevier, Amsterdam (1984); Kennett et al., *Monoclonal Antibodies* (Kennett et al., eds. pp. 365–367, Plenum Press, N.Y., 1980); de St. Groth, S. F., et al., *J. Immunol. Meth*. 35: 1–21 (1980); Galfre, G. et al., *Methods Enzymol*. 73:3–46 (1981); Goding, J. W. 1987. *Monoclonal Antibodies: Principles and Practice*. 2nd ed. Academic Press, London, 1987);

Fusion partner cell lines and methods for fusing and selecting hybridomas and screening for mAbs are well known in the art (Hartlow, E. et al., supra; Kawamoto, T. et al., *Meth. Enzymol* 121:266–277 (1986); Kearney, J. F. et al., *J. Immunol*. 123:1548–1550 (1979); Kilmartin, J. V. et al., *J. Cell Biol*. 93:576–582 (1982); Kohler, G. et al., *Eur. J. Immunol*. 6:292–295 (1976); Lane, D. P. et al., *J. Immunol. Meth*. 47:303–307 (1981); Mueller, U. W. et al., *J. Immunol. Meth*. 87:193–196 (1986); Pontecorvo, G., *Somatic Cell Genet*. 1:397–400 (1975); Sharo, J., et al., *Proc. Natl. Acad. Sci. USA* 76:1420–1424 (1979); Shulman, M. et al., *Nature* 276:269–270 (1978); Springer, T. A. (ed), *Hybridoma Technology in the Biosciences and Medicine*, Plenum Press, New York, 1985; and Taggart, R. T. et al., *Science* 219:1228–1230 (1982)).

Alternatively, the antibodies my be produced by culturing hybridoma or transfectoma cells in vitro and isolating secreted mAb from the cell culture medium.

PP peptide epitope related protein/gene detection and diagnostic methods. Anti-PP peptide Abs and PP peptide encoding nucleic acid probes may be used according to methods of the present invention to diagnose patients having psychotic or related disorders, or to determine relative subclinical and clinical degrees of such psychotic disorders, or predisposition thereto. The present invention is based in part on the discovery that PP peptide expression products, such as RNA and/or PP peptides, have some protective effect on psychotic disorders in humans and possibly other mammals. Accordingly, the lack of, or presence of low concentrations of, PP peptide epitope containing peptides or proteins, or PP peptide encoding nucleic acids, such as mRNA, is expected to correlate with subclinical, clinical and/or acute psychoses and related disorders, such as schizophrenia.

Therefore, diagnostic and detection methods of the present invention allow determination of the presence of, or susceptibility to, psychoses and related disorders in humans and mammals, using anti-PP peptide Abs and/or PP peptide encoding nucleic acid probes.

Antibody detection of PP peptide epitope containing proteins. Antibodies or fragments thereof having epitope binding sites specific for an epitope of a PP peptide, termed "anti-PP peptide antibodies," may be used to detect related or homologous proteins as a means to diagnose or prediagnose psychosis or related disorders, such as schizophrenia. Such antibodies or fragments may thus be used to quantitatively or qualitatively detect a protein or peptide corresponding at least in part to a PP peptide in a sample or to detect the presence of such proteins in biological fluids or cells which express such protein or peptide, in vitro, in situ, or in vivo, based on the teaching and guidance presented herein, without undue experimentation. The lack of, or presence of low concentrations of, PP peptide epitope containing peptides is expected to correlate with psychoses and related disorders, such as schizophrenia.

It will be appreciated that PP peptide antibodies, anti-idiotype antibodies and fragments thereof, such as Fab and $F(ab')_2$, may be used according to the present invention to detect and/or quantitate a PP peptide according to the methods disclosed herein for intact antibody molecules. Such fragments are typically produced by proteolytic cleavage, using enzymes such as papain (to produce Fab fragments) or pepsin (to produce $F(ab')_2$ fragments).

The antibodies of the present invention may be employed histologically, as in immunofluorescence or immunoelectron microscopy, for in situ detection of a PP peptide or a protein having psychosis protecting activity. Through the use of such a procedure, it is possible to determine not only the presence of a PP peptide or a protein having psychosis protecting activity, but also its distribution on the examined tissue.

Additionally, the antibody of the present invention can be used to detect the presence of a soluble PP peptide or a protein having psychosis protecting activity, in a biological sample, such as a means to monitor the presence and quantity of a PP peptide or a protein having psychosis protecting activity, used for diagnosis of the extent, susceptibility or degree of psychosis or related disorder.

Such immunoassays, for detecting a PP peptide, or a protein having a PP peptide epitope, typically comprise incubating a biological sample, such as a biological fluid, a tissue extract, freshly harvested cells such as lymphocytes or leukocytes, or cells which have been incubated in tissue culture, in the presence of a detectably labeled antibody capable of identifying a PP peptide, and detecting the antibody by any of a number of techniques well-known in the art. See, e.g., Ausubel, supra, Harlow, supra.

The biological sample may be treated with a solid phase support or carrier (which terms are used interchangeably herein) such as nitrocellulose, or other solid support which is capable of immobilizing cells, cell particles or soluble proteins. The support may then be washed with suitable buffers followed by treatment with the detectably labeled PP peptide-specific antibody. The solid phase support may then be washed with the buffer a second time to remove unbound antibody. The amount of bound label on said solid support may then be detected by conventional means.

Such detection can be accomplished by any appropriate known method steps for detecting bound antibodies, such as enzyme linked immunosorbent assays (ELISA), isotope labeling, immunodiffusion assays, immunoaffinity chromatography, immunopreciptiation, protein staining, immunoblotting, iodination of proteins, biosynthetic labeling, or, e.g., immunofluorescence techniques employing a fluorescently labeled antibody (see below) coupled with light microscopic, flow cytometric, or fluorometric detection. See, e.g., Coligan et al., supra, at Ch. 2, 5, 7 and 8; Ausubel, supra, and Harlow, supra, which references are entirely incorporated herein by reference.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, or cylindrical, as in the inside surface of a test tube, or the external surface of a rod. Alternatively, the surface may be flat such as a sheet, polymer test strip, etc. Preferred supports or carriers include polystyrene beads. Those skilled in the art will know many other suitable carriers for binding antibody or antigen, or will be able to ascertain the same by use of routine experimentation. See Coligan, supra, at Ch. 8–9.

The binding activity of a given lot of anti-PP peptide antibody may be determined according to well known method steps. Those skilled in the art will be able to determine operative and optimal assay conditions for each determination by employing routine experimentation. See, e.g., Harlow, supra, Coligan, supra, at Ch. 8. Other such steps as washing, stirring, shaking, filtering and the like may be added to the assays as is customary or necessary for the particular situation.

One of the ways in which a PP peptide-specific antibody, anti-idiotype antibody or fragment thereof, can be detectably labeled is by linking the same to an enzyme and use in an enzyme immunoassay (EIA), according to known method steps. See Harlow, supra. Coligan, supra, at Ch.2.

Detection may be accomplished using any of a variety of other immunoassays. For example, by radioactivity labeling the antibodies or antibody fragments, it is possible to detect R-PTPase through the use of a radioimmunoassay (RIA). A good description of RIA maybe found in *Laboratory Techniques and Biochemistry in Molecular Biology*, by Work et al., North Holland Publishing Company, N.Y. (1978) with particular reference to the chapter entitled "*An Introduction to Radioimmune Assay and Related Techniques*" by Chard, incorporated entirely by reference herein. The radioactive isotope can be detected by such means as the use of a γ-counter, a scintillation counter or by autoradiography.

It is also possible to label an anti-PP peptide antibody, anti-idiotype antibody or fragment thereof, with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine, commercially available, e.g., from Molecular Probes, Inc. (Eugene, Oreg.). See, e.g., Ausubel, supra, Harlow, supra, Coligan, supra, at Ch. 2 and 5.

The antibody can also be detectably labeled using fluorescence emitting metals such as $^{152}$EU, or others of the lanthanide series. These metals can be attached to the antibody using such metal chelating groups as diethylenetriamine pentaacetic acid (EDTA). See, e.g., Ausubel, supra, Harlow, supra, Coligan, supra, at § 5.3.

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in a immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody. See, e.g., Harlow, supra, and Coligan, supra, § 9.1.

Synthetic production of psychosis protecting peptides of the present invention. PP peptides and muteins can be synthesized according to known method steps. Chemical polypeptide synthesis is a rapidly evolving area in the art, and methods of solid phase polypeptide synthesis are well-described in the following references, hereby entirely incorporated by reference: (Merrifield, B., *J. Amer. Chem. Soc.* 85:2149–2154 (1963); Merrifield, B., *Science* 232:341–347 (1986); Wade, J. D. et al., *Biopolymers* 25:S21–S37 (1986); Fields, G. B., *Int. J. Polypeptide Prot. Res.* 35:161 (1990); MilliGen Report Nos. 2 and 2a, Millipore Corporation, Bedford, Mass., 1987) Ausubel, supra, Sambrook et al, supra, Coligan, supra, Ch. 9, which references are all entirely incorporated herein by reference.

In general, as is known in the art, such methods involve blocking or protecting reactive functional groups, such as free amino, carboxyl and thio groups. After peptide bond formation, the protective groups are removed (or de-protected). Thus, the addition of each amino acid residue requires several reaction steps for protecting and deprotecting. Current methods utilize solid phase synthesis, wherein the C-terminal amino acid is covalently linked to an insoluble resin particle large enough to be separated from the fluid phase by filtration. Thus, reactants are removed by washing the resin particles with appropriate solvents using an automated programmed machine. The completed polypeptide chain is cleaved from the resin by a reaction which does not affect polypeptide bonds.

More recently, the preferred "Fmoc" technique has been introduced as an alternative synthetic approach, offering milder reaction conditions, simpler activation procedures and compatibility with continuous flow techniques. This method was used, e.g., to prepare the peptide sequences disclosed in the present application. Here, the α-amino group is protected by the base labile 9-fluorenylmethoxycarbonyl (Fmoc) group. The benzyl side chain protecting groups are replaced by the more acid labile t-butyl derivatives. Repetitive acid treatments are replaced by deprotection with mild base solutions, e.g., 20% piperidine in dimethylformamide (DMF), and the final HF cleavage treatment is eliminated. A TFA solution is used instead to cleave side chain protecting groups and the polypeptide resin linkage simultaneously.

At least three different polypeptide-resin linkage agents can be used: substituted benzyl alcohol derivatives that can be cleaved with 95% TFA to produce a polypeptide acid, methanolic ammonia to produce a polypeptide amide, or 1% TFA to produce a protected polypeptide which can then be used in fragment condensation procedures, as described by Atherton, E. et al., *J. Chem. Soc. Perkin Trans.* 1:538–546 (1981) and Sheppard, R. C. et al., *Int. J. Polypeptide Prot.*

*Res*. 20:451–454 (1982). Furthermore, highly reactive Fmoc amino acids are available as pentafluorophenyl esters or dihydro-oxobenzotriazine esters derivatives, saving the step of activation used in the tBoc method.

Recombinant production of psychosis protecting peptides of the present invention. Sequences available to use as a basis for PP peptide synthesis can be based on amino acid and/or nucleotide sequences corresponding to SEQ ID NOs: 3–12. Recombinant production of PP peptides can be accomplished according to known method steps. Standard reference works setting forth the general principles of recombinant DNA technology include Watson, J. D. et al., *Molecular Biology of the Gene*, Volumes I and II, The Benjamin/Cummings Publishing Company, Inc., publisher, Menlo Park, Calif. (1987); Darnell, J. E. et al., *Molecular Cell Biology*, Scientific American Books, Inc., publisher, New York, N.Y. (1986); Lewin, B. M., *Genes III*, John Wiley & Sons, publishers, New York, N.Y. (1989); Old, R. W., et al., *Principles of Gene Manipulation: An Introduction to Genetic Engineering*, 2d edition, University of California Press, publisher, Berkeley, Calif. (1981); Ausubel et al, eds., supra; Sambrook, supra; Harlow, supra; and Coligan et al., supra, the entire contents of which references are herein incorporated by reference.

A nucleic acid sequence encoding a PP peptide of the present invention may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Ausubel et al, supra, and are well known in the art.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as PP peptides in recoverable amounts. The precise nature of the regulatory regions needed for gene expression may vary from organism to organism, as is well known in the analogous art. See, e.g., Sambrook, supra and Ausubel supra.

The present invention accordingly encompasses the expression of a PP peptide, in either prokaryotic or eukaryotic cells, although eukaryotic expression is preferred.

Preferred hosts are bacterial or eukaryotic hosts including bacteria, yeast, insects, fungi, bird and mammalian cells either in vivo, or in situ, or host cells of mammalian, insect, bird or yeast origin. It is preferred that the mammalian cell or tissue is of human, primate, hamster, rabbit, rodent, cow, pig, sheep, horse, goat, dog or cat origin, but any other mammalian cell may be used.

Further, by use of, for example, the yeast ubiquitin hydrolase system, in vivo synthesis of ubiquitin-transmembrane polypeptide fusion proteins may be accomplished. The fusion proteins so produced may be processed in vivo or purified and processed in vitro, allowing synthesis of a PP peptide of the present invention with a specified amino terminus sequence. Moreover, problems associated with retention of initiation codon-derived methionine residues in direct yeast (or bacterial) expression may be avoided. Sabin et al., *Bio/Technol*. 7(7): 705–709 (1989); Miller et al., *Bio/Technol*. 7(7): 698–704 (1989).

Any of a series of yeast gene expression systems incorporating promoter and termination elements from the actively expressed genes coding for glycolytic enzymes produced in large quantities when yeast are grown in mediums rich in glucose can be utilized to obtain PP peptides of the present invention. Known glycolytic genes can also provide very efficient transcriptional control signals. For example, the promoter and terminator signals of the phosphoglycerate kinase gene can be utilized.

Production of PP peptides or functional derivatives thereof in insects can be achieved, for example, by infecting the insect host with a baculovirus engineered to express at least one PP peptide by methods known to those of skill. See Ausubel, supra, at §§16.8–16.11.

In a preferred embodiment, the introduced nucleotide sequence will be incorporated into a plasmid or viral vector capable of autonomous replication in the recipient host. Any of a wide variety of vectors may be employed for this purpose. See, e.g., Ausubel et al, supra, §§ 1.5, 1.10, 7.1, 7.3, 8.1, 9.6, 9.7, 13.4, 16.2, 16.6, and 16.8–16.11. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors known in the art include plasmids such as those capable of replication in *E. coli* (such as, for example, pBR322, ColE1, pSC101, pACYC 184, πVX). Such plasmids are, for example, disclosed by Maniatis, T., et al. (*Molecular Cloning*, A Laboratory Manual, Second Edition, Cold Spring Harbor Press, Cold Spring Harbor, N.Y. (1989); Ausubel et al, eds., supra. Bacillus plasmids include pC194, pC221, pT127, etc. Such plasmids are disclosed by Gryczan, T. (In: *The Molecular Biology of the Bacilli*, Academic Press, N.Y. (1982), pp. 307–329). Suitable Streptomyces plasmids include pIJ101 (Kendall, K. J., et al., *J. Bacteriol*. 169:4177–4183 (1987)), and streptomyces bacteriophages such as φC31 (Chater, K. F., et al., In: *Sixth International Symposium on Actinomycetales Biology*, Akademiai Kaido, Budapest, Hungary (1986), pp. 45–54). Pseudomonas plasmids are reviewed by John, J. F., et al. (*Rev. Infect. Dis*. 8:693–704 (1986)), and Izaki, K. (Jpn. *J. Bacteriol*. 33:729–742 (1978); and Ausubel et al, supra).

A gene or nucleic acid encoding for a naturally occurring protein having a PP peptide sequence can also be detected, obtained and/or modified, in vitro, in situ and/or in vivo, by the use of known DNA or RNA amplification techniques, such as PCR and chemical oligonucleotide synthesis. PCR allows for the amplification (increase in number) of specific DNA sequences by repeated DNA polymerase reactions. This reaction can be used as a replacement for cloning, all that is required is a knowledge of the nucleic acid sequence. In order to carry out PCR, primers are designed which are complementary to the sequence of interest, such as a 10–140 base sequence as presented in SEQ ID NO:3. The primers are then generated by automated DNA synthesis. Because primers can be designed to hybridize to any part of the gene, conditions can be created such that mismatches in complementary base pairing can be tolerated. Amplification of these mismatched regions can lead to the synthesis of a mutagenized product resulting in the generation of a peptide with new properties (i.e., site directed mutagenesis). See also, e.g., Ausubel, supra, Ch. 16, and Coligan, supra, at §§ 10.20–10.23. Also, by coupling complementary DNA (cDNA) synthesis, using reverse transcriptase, with PCR, RNA can be used as the starting material for the synthesis of the PP gene without cloning. Detection of PCR and other methods of amplification of RNA and/or DNA are well known in the art and can be used according to the present invention without undue experimentation, based on the teaching and guidance presented herein. Known methods of DNA or RNA amplification include, but are not limited to polymerase chain reaction (PCR) and related amplification processes (see, e.g., U.S. Pat. Nos. 4,683,195, 4,683,202, 4,800,159, 4,965,188, to Mullis et al.; 4,795,699 and 4,921,794 to Tabor et al; 5,142,033 to Innis; 5,122,464 to Wilson et al.; 5,091,310 to Innis; 5,066,584 to Gyllensten et al; 4,889,818 to Gelfand et al; 4,994,370 to Silver et al; 4,766,067 to Biswas; 4,656,134 to Ringold; and Innis et al eds. PCR Protocols: A Guide to Method and Applications) and RNA mediated amplification which uses anti-sense RNA to the target sequence as a template for double stranded DNA synthesis (U.S. Pat. No. 5,130,238 to Malek et al, with the tradename NASBA); and immuno-PCR which combines the use of DNA amplification with antibody labeling (Ruzicka et al., *Science* 260:487 (1993); Sano et al, *Science* 258:120 (1992); Sano et al., *Biotechniques* 9:1378 (1991)), entire contents of which patents and reference are entirely incorporated herein by reference.

PP peptide antibody purification. The expressed protein may be isolated and purified in accordance with known method steps, such as extraction, precipitation, chromatography, affinity chromatography, electrophoresis, or the like. For example, the cells may be collected by centrifugation, or with suitable buffers, lysed, and the protein isolated by column chromatography, for example, on DEAE-cellulose, phosphocellulose, polyribocytidylic acid-agarose, hydroxyapatite or by electrophoresis or immunoprecipitation. Alternatively, the PP peptide or mutein thereof may be isolated by the use of anti-PP peptide antibodies. Such antibodies may be obtained by well-known methods, some of which are mentioned below. These antibodies may be immobilized on cellulose, agarose, hollow fibers, or cellulose filters by covalent chemical derivatives by methods well known to those skilled in the art. See, e.g., Harlow, supra, Coligan, supra, Ausubel, supra.

As discussed herein, PP peptides of the present invention may be further modified for purposes of drug design, such as for example to reduce immunogenicity, to prevent solubility and/or enhance delivery, or to prevent clearance or degradation.

Appropriate modification of the primary amino acid sequence of PP peptides of the present invention, obtained by mutagenesis or utilizing fragments, as described herein, will allow the creation of molecules which affect psychosis related symptoms than that exhibited by naturally psychosis protecting proteins. Small polypeptides that are provided according to the present invention which polypeptides maintain psychosis protecting activity, are expected to have two advantages over larger polypeptides. These advantages include (1) greater stability and diffusibility, and (2) less immunogenicity.

Pharmaceutical Preparations and Administration

Preparations of PP peptides for parenteral administration include sterile aqueous or non-aqueous solutions, suspensions, and emulsions, which may contain auxiliary agents or excipients which are known in the art. Pharmaceutical compositions such as tablets and capsules can also be prepared according to routine methods.

By the term "protection" from infection or disease as used herein is intended "prevention," "suppression" or "treatment." "Prevention" involves administration of a PP peptide or anti-idiotypic antibody prior to the induction of the disease.

"Suppression" involves administration of the composition prior to the clinical appearance of the disease.

"Treatment" involves administration of the protective composition after the appearance of the disease. It will be understood that in human and veterinary medicine, it is not always possible to distinguish between "preventing" and "suppressing" since the ultimate inductive event or events may be unknown, latent, or the patient is not ascertained until well after the occurrence of the event or events. Therefore, it is common to use the term "prophylaxis" as distinct from "treatment" to encompass both "preventing" and "suppressing" as defined herein. The term "protection," as used herein, is meant to include "prophylaxis."

At least one PP peptide, antibody or anti-idiotypic antibody of the present invention may be administered by any means that achieve their intended purpose, for example, to treat PP related pathologies, such as psychotic disorders, including schizophrenia using a PP peptide alone or preferably in the form of a pharmaceutical composition.

For example, administration of such a composition may be by various parenteral routes such as subcutaneous, intravenous, intradermal, intramuscular, intraperitoneal, intranasal, transdermal, or buccal routes. Alternatively, or concurrently, administration may be by the oral route. Parenteral administration can be by bolus injection or by gradual perfusion over time.

A preferred mode of using a PP pharmaceutical composition of the present invention is by intravenous or parenteral application.

A typical regimen for preventing, suppressing, or treating schizophrenia related symptoms or symptoms of other psychoses, comprises administration of an effective amount of a PP peptide administered over a period of one or several days, up to and including between one week and about 24 months.

It is understood that the dosage of a PP peptide of the present invention administered in vivo or in vitro will be dependent upon the age, sex, health, and weight of the recipient, kind of concurrent treatment, if any, frequency of treatment, and the nature of the effect desired. The ranges of effective doses provided below are not intended to limit the inventors and represent preferred dose ranges. However, the most preferred dosage will be tailored to the individual subject, as is understood and determinable by one of skill in the art, without undue experimentation.

The total dose required for each treatment may be administered by multiple doses or in a single dose. A PP peptide or functional a chemical derivative thereof may be administered alone or in conjunction with other therapeutics directed to schizophrenia related disorders or other symptoms of the disorder.

Effective amounts of the PP peptide or composition, or a PP anti-idiotypic antibody, are from about 0.01 $\mu$g to about 100 mg/kg body weight, and preferably from about 10 $\mu$g to about 50 mg/kg body weight, such 0.05, 0.07, 0.09, 0.1, 0.5, 0.7, 0.9, 1, 2, 5, 10, 20, 25, 30, 40, 45, 50, 60, 70, 80, 90 or 100 mg/kg, or any value or range therein.

Preparations for parenteral administration include sterile aqueous or non-aqueous solutions, suspensions, and emulsions, which may contain auxiliary agents or excipients which are known in the art. Pharmaceutical compositions such as tablets and capsules can also be prepared according to routine methods.

Pharmaceutical compositions comprising at least one PP peptide of the present invention may include all compositions wherein the PP peptide is contained in an amount effective to achieve its intended purpose. In addition to the PP peptide, a pharmaceutical composition may contain suitable pharmaceutically acceptable carriers, such as comprising excipients and auxiliaries which facilitate processing of the active compounds into preparations which can be used pharmaceutically.

Pharmaceutical compositions according to the present invention may further, optionally comprise an antipsychotic, such as an therapeutic agent selected from the group consisting of a phenothiazine derivative, a thioxanthine derivative, a butyrophenone derivative, a dihydroindolone, a dibenzoxazepine derivative and an atypical neuroleptic (see, e.g., Baldessarini, supra, Katzung, supra).

Pharmaceutical compositions include suitable solutions for administration intravenously, subcutaneously, dermally, orally, mucosally, rectally or may by injection or orally, and contain from about 0.01 to 99 percent, preferably from about 20 to 75 percent of active component (i.e. the antibody) together with the excipient. Pharmaceutical compositions for oral administration include tablets and capsules. Compositions which can be administered rectally include suppositories.

Transgenic Animals. Animal models of psychoses, such as schizophrenia may now be provided according to the present invention by the use of transgenic animals that are inhibited (as psychosis model) or consitutively express (as normal controls) PP peptide related proteins.

The present invention is thus also directed to a transgenic non-human eukaryotic animal (preferably a rodent, such as a rat or mouse) whose germ cells and somatic cells contain genomic DNA according to the present invention which codes for antisense or inhibiting expression products which prevent the expression of PP peptide related proteins having a psychotic protecting effect in normal mammals. Such inhibiting nucleic acids may be introduced into the animal, or an ancestor of the animal, at an embryonic stage, preferably the one-cell, or fertilized oocyte, stage, and generally not later than about the 8-cell stage. The activated sequence, as the term is used herein, means a gene which, when incorporated into the genome of the animal, is expressed in the animal and increases the probability of the development of a psychosis or related disorder in the animal.

There are several means by which such a inhibiting nucleic acid can be introduced into the genome of the animal embryo so as to be chromosomally incorporated and expressed. One method is to transfect the embryo with the gene as it occurs naturally, and select transgenic animals in which the gene has integrated into the chromosome at a locus which results in expression. Other methods for ensuring expression involve modifying the gene or its control sequences prior to introduction into the embryo. One such method is to transfect the embryo with a vector (see above) containing an already modified gene. Other methods are to use a gene the transcription of which is under the control of a inducible or constitutively acting promoter, whether synthetic or of eukaryotic or viral origin, or to use a gene activated by one or more base pair substitutions, deletions, or additions (see above).

Introduction of the desired gene sequence at the fertilized oocyte stage ensures that the transgene is present in all of the germ cells and somatic cells of the transgenic animal and has the potential to be expressed in all such cells. The presence of the transgene in the germ cells of the transgenic "founder" animal in turn means that all its progeny will carry the transgene in all of their germ cells and somatic cells. Introduction of the transgene at a later embryonic stage in a founder animal may result in limited presence of the transgene in some somatic cell lineages of the founder; however, all the progeny of this founder animal that inherit the transgene conventionally, from the founder's germ cells, will carry the transgene in all of their germ cells and somatic cells.

Chimeric non-human mammals in which fewer than all of the somatic and germ cells contain the desired PP peptide related protein inhibiting nucleic acid, produced, for example, when fewer than all of the cells of the morula are transfected in the process of producing the transgenic mammal, are also intended to be within the scope of the present invention.

The techniques described in Leder, U.S. Pat. No. 4,736,866, for producing transgenic non-human mammals may be used for the production of the transgenic non-human mammal of the present invention. The various techniques described in Palmiter et al., *Ann. Rev. Genet.*, 20, 465–99 (1986), the entire contents of which are hereby incorporated by reference, may also be used.

The animals carrying this gene can be used to test compounds which may affect the progress of psychotic disorders or to test compounds which may be used to prevent the development of psychoses in susceptible patients. These tests can be extremely sensitive because of the propensity of these transgenic animals to develop psychotic disorders. Such animals will also serve as an animal model enabling testing of treatment and diagnostic methods for all psychotic disorders to be performed on non-humans. Transgenic animals according to the present invention can also be used as a source of cells for cell culture.

Muteins of PP peptides of the present invention may include peptides which are distinct from PP peptides discussed above in critical structural features, but which maintain anti-schizophrenia biological activity. Such consensus peptides may be derived by molecular modeling, optionally combined with hydrophobicity analysis and/or fitting to model helices, as non-limiting examples. Such modeling can be accomplished according to known method steps using known modeling algorithms, such as, but not limited to, ECEPP, INSIGHT, DISCOVER, CHEM-DRAW, AMBER, FRODO and CHEM-X.

Such consensus peptides or fragments of PPs may then be synthesized or produced recombinantly, in order to provide PP peptides according to the present invention which have anti-schizophrenia or inhibit the biological activity.

In addition, any amide linkage in any of the PP peptides can be replaced by a ketomethylene moiety, e.g. (—C(=O)—$CH_2$—) for (—(C=O) —NH—). Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

In addition, any amino acid representing a component of the said peptides can be replaced by the same amino acid but of the opposite chirality. Thus, any amino acid naturally occurring in the L-configuration (which may also be referred to as the R or S, depending upon the structure of the chemical entity) may be replaced with an amino acid of the same chemical structural type, but of the opposite chirality, generally referred to as the D- amino acid but which can additionally be referred to as the R- or the S-, depending upon its composition and chemical configuration. Such derivatives have the property of greatly increased stability to degradation by enzymes, and therefore are advantageous in the formulation of compounds which may have longer in vivo half lives, when administered by oral, intravenous, intramuscular, intraperitoneal, topical, rectal, intraocular, or other routes.

Additional amino acid modifications of amino acids of PP peptides of to the present invention may include the following: Cysteinyl residues may be reacted with alpha-haloacetates (and corresponding amines), such as 2-chloroacetic acid or chloroacetamide, to give carboxymethyl or carboxyamidomethyl derivatives. Cysteinyl residues may also be derivatized by reaction with compounds such as bromotrifluoroacetone, alpha-bromo- beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with compounds such as diethylprocarbonate e.g., at pH 5.5–7.0 because this agent is relatively specific for the histidyl side chain, and para-bromophenacyl bromide may also be used; e.g., where the reaction is preferably performed in 0.1 M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues. Other suitable reagents for derivatizing alpha-amino-containing residues include compounds such as imidoesters/ e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues per se is well-known, such as for introducing spectral labels into tyrosyl residues by reaction with aromatic diazonium compounds or tetranitromethane. N-acetylimidizol and tetranitromethane may be used to form O-acetyl tyrosyl species and 3-nitro derivatives, respectively.

Carboxyl side groups (aspartyl or glutamyl) may be selectively modified by reaction with carbodiimides (R'—N—C—N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues may be converted to asparaginyl and glutaminyl residues by reaction with ammonium ions.

Glutaminyl and asparaginyl residues may be frequently deamidated to the corresponding glutamyl and aspartyl residues. Alternatively, these residues may be deamidated under mildly acidic conditions. Either form of these residues falls within the scope of the present invention.

Derivatization with bifunctional agents is useful for cross-linking the peptide to a water-insoluble support matrix or to other macromolecular carriers, according to known method steps. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photo-activatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 (which are herein incorporated entirely by reference), may be employed for protein immobilization.

Other modifications of PP peptides of the present invention may include hydroxylation of proline and lysine, phosphorylation of hydroxyl groups of seryl or threonyl residues, methylation of the alpha-amino groups of lysine, arginine, and histidine side chains (T. E. Creighton, *Proteins: Structure and Molecule Properties*, W.H. Freeman & Co., San Francisco, pp. 79–86 (1983)), acetylation of the N-terminal amine, methylation of main chain amide residues (or substitution with N-methyl amino acids) and, in some instances, amidation of the C-terminal carboxyl groups, according to known method steps.

Such derivatized moieties may improve the solubility, absorption, permeability across the blood brain barrier biological half life, and the like. Such moieties or modifications of PP peptides may alternatively eliminate or attenuate any possible undesirable side effect of the protein and the like. Moieties capable of mediating such effects are disclosed, for example, in *Remington's Pharmaceutical Sciences*, 16th ed., Mack Publishing Co., Easton, Pa. (1980).

Such chemical derivatives of PP peptides also may provide attachment to solid supports, including but not limited to, agarose, cellulose, hollow fibers, or other polymeric carbohydrates such as agarose, cellulose, such as for purification, generation of antibodies or cloning; or to provide altered physical properties, such as resistance to enzymatic degradation or increased binding affinity or modulation for PP peptides, which is desired for therapeutic compositions comprising PP peptides, antibodies thereto or fragments thereof. Such peptide derivatives are well-known in the art, as well as method steps for making such derivatives using carbodiimides active esters of N-hydroxy succinimide, or mixed anhydrides, as non-limiting examples.

Variation upon consensus peptide sequences of PP peptide of the present invention may also include: the addition of one, two, three, four, or five lysine, arginine or other basic residues added to the —COOH terminal end of the peptide; and/or one, two, three, four, or five glutamate or aspartate or other acidic residues added to the amino terminal end of the peptide, where "acidic" and "basic" are as defined herein. Such modifications are well known to increase the a-helical content of the peptide by the "helix dipole effect". They also can provide enhanced aqueous solubility of the peptide. See, e.g., Baldwin et al., supra.

PP peptides of the present invention also include peptides having un-natural amino acids by exploiting a phenomenon known as suppression. Some bacteria, when encountering a nonsense mutation (e.g., an internal stop codon: UAA, UAG, UGA) substitutes an amino acid using a charged transfer RNA that carries the proper anticodon to allow for translocation in spite of the error in RNA sequence (i.e. suppression). By charging the suppressor to RNA with an unnatural amino acid, peptides can be generated with specific substitutions through modification during translation.

Having now generally described the invention, the same will be more readily understood through reference to the following example which is provided by way of illustration, and is not intended to be limiting of the present invention.

EXAMPLE 1

Isolation of a PP Peptide Encoding Gene from Monozygotic Twins Discordant for Schizophrenia Monozygotic twins discordant for schizophrenia represent excellent subjects to assay for differences in gene expression at the transcriptional level. The assumption is that variance in phenotype (in this case mental function) is attributable to the way in which the genetic potential is expressed. Removal of commonly expressed transcripts by subtractive hybridization should result in enrichment of phenotype specific gene products even when these transcripts are at less than 0.05% of the total in mRNA population (Travis et al, 1987).

The logical tissue source for these studies is the brain; however, because of our interest in living subjects, an alternative tissue, the peripheral blood lymphocyte was used. While seeming counter-intuitive, it is possible to show that gene expression in an accessible tissue in which a gene has no function may serve to monitor expression in an inaccessible tissue in which the function of the gene product has physiological significance (Chelly et al 1988). Accordingly, we have demonstrated that a subtracted clone obtained from the lymphocytes of a discordant schizophrenic twin pair is expressed in the CNS of rats.

Materials and Methods

The subjects for this study were 64 year old female monozygotic twins discordant for schizophrenia (DSMIIIR). The schizophrenic co-twin had been neuroleptic free for more than 30 years. Lymphocytes from 250 cc of whole blood were isolated by separation on Ficoll-Paque according to the manufacturers' instructions. RNA isolation, cDNA synthesis and cDNA cloning were accomplished as described by Belyavsky et al., *Nucl. Acids Res.* 17:2919–2932 (1989), with minor modifications. A cDNA library was made for each twin and subtractive hybridization was achieved as described in the manual provided in the Subtractor II Kit manufactured by InVitrogen. Libraries were screened with (32p) labeled cDNA using the +/− method for differential clone identification and subsequent isolation. Probes for in situ hybridization were synthesized by in vitro transcription with T7 (anti-sense) and SP6 RNA (sense) polymerases in the presence of (33p) labeled UTP, using the subtracted clone as the template. The use of the (33p) labeled results in greater resolution and shorter exposure time as compared to (35s) labeled isotopes.

RESULTS

Figure 2:
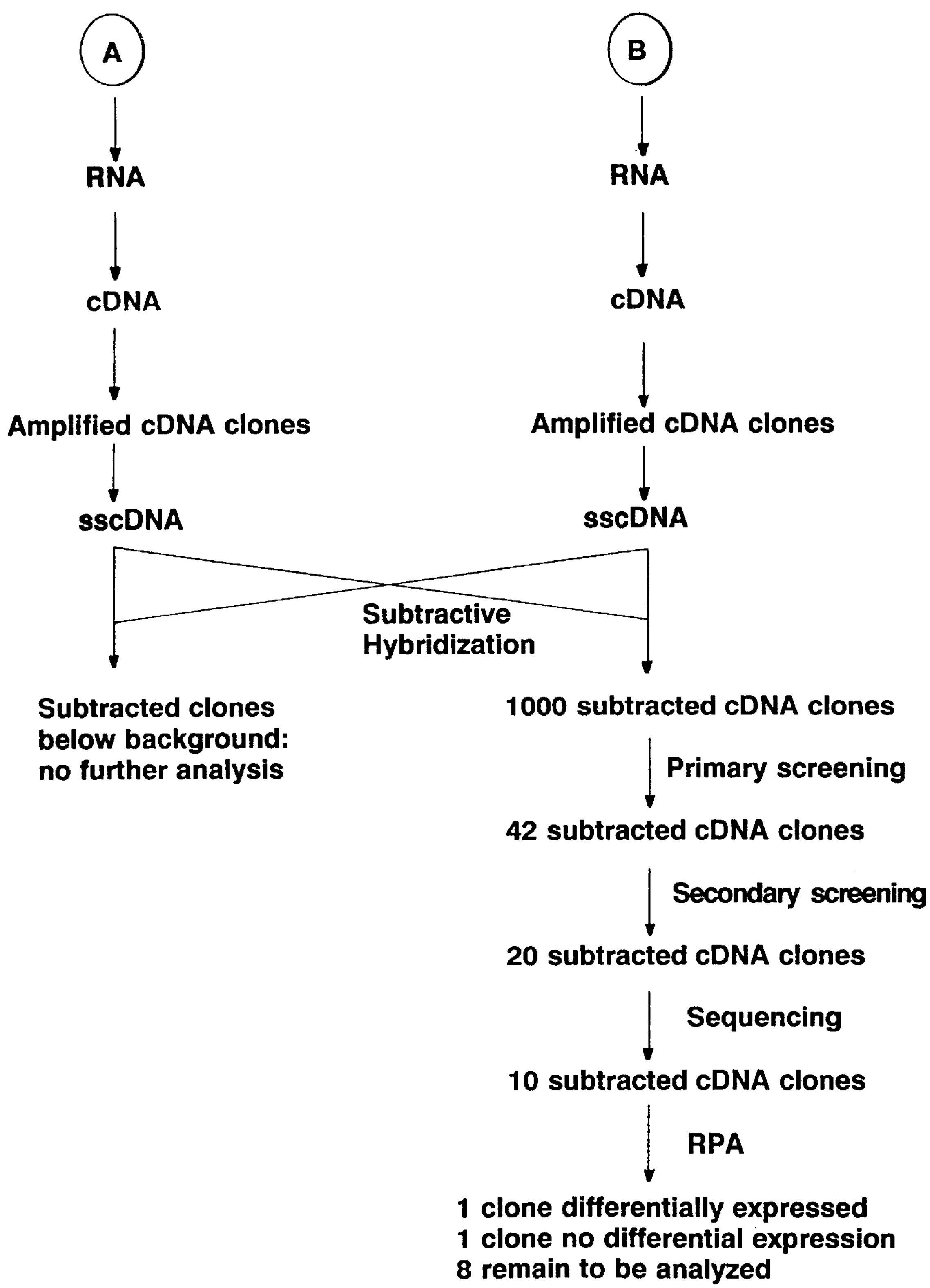
FIG. 2 is a subtraction cloning scheme used to detect subtracted clones used to obtain a schizophrenia protection gene according to the present invention.

A flow chart of the procedures used to detect the subtracted clones is shown in FIG. 2. Because we did not know, a priori, in which subject we would observe differential expression, both libraries had to be used as driver and substrate in two separate subtraction assays.

The number of subtracted clones identified in the assay where the "sick" twin's cDNA was used in excess was within the 2% background value determined previously. However, when the cDNA of the "well" twin was used in excess, the number of differential clones was approximately 4%. We isolated 41 clones for further analysis based on the results of the primary screening. Secondary screening of the clones reduced the number to 20. These twenty clones were then used for mini plasmid preparations and subsequently sequenced. After sequencing the number of clones was reduced to 10.

In order to verify that subtracted clones were differentially expressed we employed an RNase protection assay (RPA). RPA results demonstrated that out of the two clones tested thus far, one clone (pOKSC4c) was differentially expressed. The expression of the clone was greatest for the "well" twin.

The fact that this clone was expressed in the well twin but not the sick is consistent with our conclusion that his gene serves a protective function in the well twin. If as shown earlier schizophrenia is a genetic disorder, both monozygotic twins carry the schizophrenia gene. The well twin expresses pOKSC4c while the schizophrenic twin does not; therefore pOKSC4c must be protecting the well twin from the deleterious effects of the schizophrenia gene.

In this case pOKSC4c is protecting against schizophrenia. In other patients genetically vulnerable to psychoses other than schizophrenia or vulnerable to other causes of psychosis, pOKSC4c could be expressed to protect against these psychoses. Thus, although pOKSC4c was isolated from twins discordant for schizophrenia, this in no way limits the protective effect of PP peptide to schizophrenia.

Figure 3A:
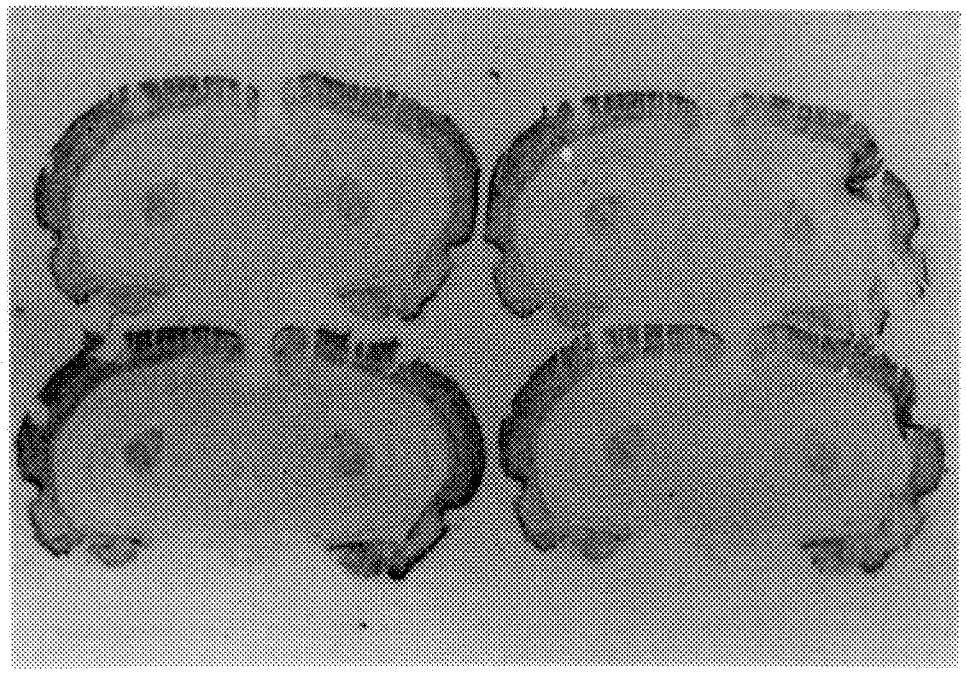
FIGS. 3A–B are pictorial representations of in situ autoradiographies showing (FIG. 3A) hybridization of a psychosis protecting gene of the present invention with cortex and medial geniculate nuclei, including the CA1 to CA3 of Ammon's horn (hippocampus), with the interrhinal, perirhinal and temporal cortexes having higher signals.
Figure 3B:
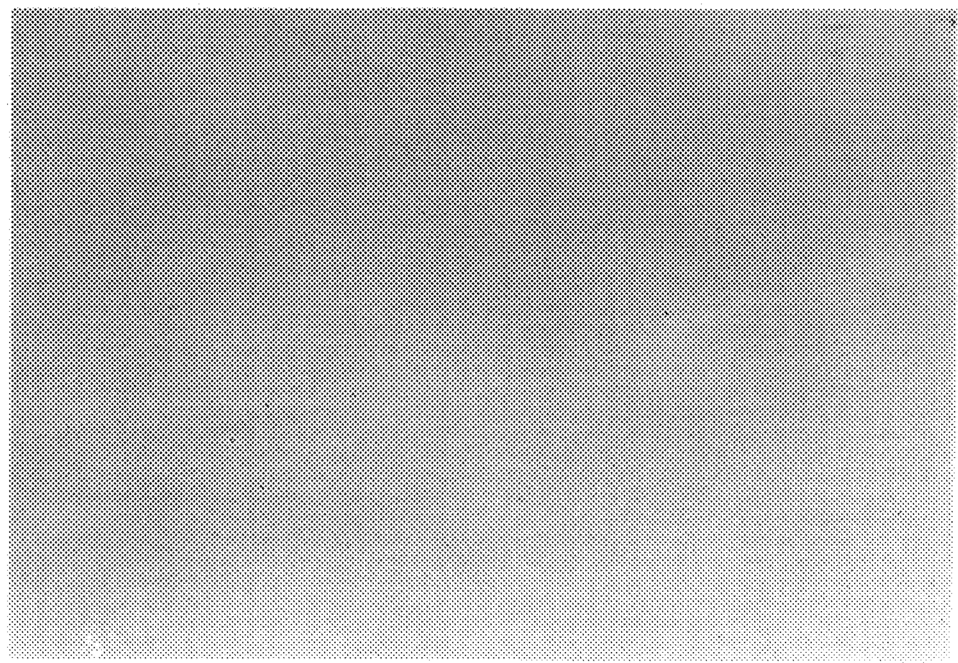

In situ hybridization studies were carried out to determine if pOSKC4c was expressed in rat brain. Examination of the in situ audioradiograph (FIG. 3A) reveals that the two most intense regions of hybridization are: 1) the cortex and 2) the medial geniculate nucleus. CAI to CA3 of Ammon's horn (hippocampus) also hybridize to the clone. The hybridization signal in the cortex seems to be qualitatively higher in certain cortical regions. As seen in FIG. 3A, the interhinal cortex, perirhinal cortex and temporal cortex (areas 1 and 3) give a more intense signal than the rest of the cortex. Lastly, these details were completely absent when the sense strand was used as a control (FIG. 3B).

DISCUSSION

Chelly et al., supra (1988), using quantitative PCR, found that dystrophin message could be detected in lymphocytes from normal subjects but not in lymphocytes of subjects with Duchenne's muscular dystrophy. For the dystrophin gene, at least, a very low level of expression of the gene occurs in lymphocytes even though the gene product, dystrophin, has a function in muscle but not in blood cells. Thus the dystrophin gene appears to "dribble" a very low level of RNA in the lymphocyte, whereas the mutant gene does not "dribble" in lymphocytes of the DMD subjects.

As described above, the probe derived from lymphocytes via subtractive hybridization produces a strong signal in rat cortex and geniculate body. The selective nature of the hybridization in rat brain supports the idea that this gene may be associated with specific functions in the brain rather than be ubiquitously active.

Subtracted cDNA Clones from a Monozygotic Twin Pair Discordant for Schizophrenia pOKSC4c pOKSC4c: The plasmid contains a 371 bp fragment, encoding what seems to be the 3' end of a previously unreported gene, which has been inserted into the BamH I site of the Invitrogen plasmid pcDNA II. The orientation of the insert is such that the SP6 promoter lies at the 5' end of the gene fragment.

This plasmid was isolated by screening a subtracted cDNA library generated from the RNA of lymphocytes obtained from a set of monozygotic twins discordant for schizophrenia. The cDNA libraries used as substrate for the subtraction assay were constructed using PCR according to the method described by Belyavsky, et al., *Nucl. Acids Res.* 17:2919–2932 (1989), with slight modifications. The two oligonucleotides used in library construction are described below.

Oligonucleotide used for first strand cDNA synthesis and 3 downstream primer during amplification for all cDNAs (5' to 3' orientation): TTTTTTTTTTTTTTTTC-CCCGGGCTA* T7 promoter (SEQ ID NO:1)

*Bold characters correspond to partial BamH I restriction endonuclease recognition sites used for insertion into pcDNAII. Oligonucleotide used for 5' upstream primer during amplification for all cDNAs (5' to 3' orientation):

SP6 promoter *ATCGAAATTCCCCCCCCCCCCC (SEQ ID NO:2)

*Bold characters correspond to partial BamH I restriction endonuclease recognition sites used for insertion into pcDNAII.

Preliminary evidence using RNase protection assays provides the clear expectation that the full length gene corresponding to the pOKSC4c insert is differentially expressed in this set of twins, such that the "well twins" is expected to make significantly more of the protein encoded by the full length gene than the "sick" co-twin.

Addititionally, data have been obtained which demonstrate that the gene corresponding to the pOKSC4c fragment is expressed in rat brain. Characterization of the full length gene accordingly may be provided based on the use of probes based on or derived from SEQ ID NO:3 according to known method steps, without undue experimentation (see, e.g., Sambrook, supra, Ausubel, supra). It is also expected that fragments of this gene corresponding to the protein coding region may be used according to the present invention to provide a marker for various psychoses, such as schizophrenia, as well as a means to treat such disorders.

EXAMPLE II

Cloning and Expression of PP Peptide Related Proteins

According to the present invention, 15–45 base portions of SEQ ID NO:3 are used as oligo probes to screen genomic and cDNA libraries according to known method steps as presented in Ausubel, supra, and Sambrook, supra. Isolated clones are then expressed in suitable expression vectors in appropriate host cells and sequenced as both the DNA encoding the gene and the expressed PP peptide related protein. The protein is then purified and sequenced, and then used to generate antibodies, to generate transgenics expressing and not expressing the PP peptide or related protein, as animal models of psychoses, and as part of therapeutic compositions used for treating various psychotic disorders, such as schizophrenia, as described herein.

EXAMPLE III

Subtracted Clones Containing DNA Encoding PP Peptide Related Protein

According to the methods presented in Examples I and II above, and according to method steps known in the art, the following clones were isolated and sequenced: POKSC4c (371 bp)

This cDNA seems to be expressed in the "well" twin more abundantly than in the "sick" co-twin as determined by RPA.

This cDNA has also been shown to be expressed in the following areas of the rodent brain; cortex (RPA, Northern blot and In situ Hybridization), hippocampus (RPA and In situ hybridization) and medial geniculate nucleus (In situ hybridization).

TTTTCAGCAG TTGGCCTTTG TTGAGAAAAT GTGT-GACTTT GCCCAAGCCC AGTAACTTGG 60 AGCCT-TGAAT TTGAGATGCT GGAAAGGGAG TCCTTC-CTCC TTTCTGCAGT GTTGTCCCTA 120
GTTTACCAAA GTCCATTTTG AATGTACCAT CCCCAGCCCA ACTCCAGCCT ACAGATAGTG 180
CCAGACCGCC AGTAGGTGAG TAGCACTGTC TTC-CTGGTCC GGACCTAGTG GCTTTGCTGT 240 TAG-GACCTTA TCACTAGAGA TGGCCTGGAT TTA-GAGACGA ACCATTAGCT GTTGCCATAG 300
CTGTTGCCAT ATGATTACGT GGCCTTGGGT TTCG-CAATAA TTTATTTGGG TTCACTAAAT 360
TTTAAATTTC T 371 (SEQ ID NO:3)

POKSC25b (206 bp)

This cDNA seems to be expressed in the "well" twin more abundantly than in the "sick" cotein as determined by RPA.

TTCGTATGGA CTCGGAATAA AGTAAGTGTT TTCAGCCTGG CTGGATGTAT GTTGCAAAAT 60
GGCCTCGATT CACCCAGGGC AATAAACAGT GGTATTGATA ACCCAAAACA ATAGTAATTG 120
AAAATAATTT GTTTTAAAAG TATATGCTTT TCTTTTGATA CTCAAGTGTT TCATATTAGA 180
GGTAAATGAG AAAATATAGA TGAACC 206 (SEQ ID NO:4)

pOKSC27c (110 bp)

TTTGGAAGAT TTATTAATTG ATTAAGGACT AGGAG-GTCCA GCTAAAATGC AATTGGATTT 60 ATTAAGG-TAC TTAAATCCAG ATTTAAGGTA TGAAATCAAG AATGGCGAAC 110 (SEQ ID NO:5)

Seems to be expressed in the "well" twin more abundantly than in the "sick" co-twin as determined by RPA. Preliminary analysis suggests that it is also expressed in rat brain (Northern blot).

TCCAAGAACA GTTTTGGGCC AAACAGACGA ACAGCCAGTT GGTTTTCTAT ACCAACTGTG 60
TGATTTATTA GAGCTGTCAC ATGCTATCAT GAACT-GCGCT GTACGAAGTC AACTCAGTGA 120 TGATGT-GAGG TATCACTACT AGTTGGTTGG TTGGTTACAT ATCTTAAATA TGTAGACAAC 180
TTACCAACTG GAATGTTCAG CTAGCTAATA TCTCAATTAG AATC-CATCTC ACTAGGAATG 240 GGCAAACACT TGTGT-TCTAA AGTTACTTGA AAGTAGTTTA TACTGCCAAC TTGATATATA 300
TCATGCTATA GTTTGAACAT TTTGTGTACT TCCAAAATTC ACATTAAAAT CTAATCCAC 359 (SEQ ID NO:6)

TTTAGTTAGC TGGGCCTACA GGCATGCACC ACCACCATTG GCTAAGTTTT GTATTTTCAG 60
TAGAGACAGG GTTCACCATG TTGGCCAGGC TGCTCTTGAA CTCCTGACCT CAAGTGATCC 120
ACCTACCTCC GCCTCCGAAA AGTGCTAGGA TTA-CAGGCCT GAGCCACTGT GCCTGGCCTG 180
ATAAAGCACA TTTAAAGATC T 201 (SEQ ID NO:7)

pOKSC18a (45 bp)

ATTGCACTCC ATCCAGCCTG GGCAACAAGA GAGAAACTCC ATCTC 45 (SEQ ID NO:8)

pOKSC37a (174 bp)

TGTCTCTAGT AAAAATACAA AAATTGGCCG AGCGTGAAGG CTGGCGCCTC TAATCCCAGC 60
TTCTTGGGAA GCTGAGGGAA GCTGAGGCAC AAGAATTTGC TTGAGCCCAC GAGTGGTTGA 120
ATGCCAGGAC CTGTCCACTG CACTCCAGCC TGGGCGACAG AACGACACTG TCTC 174 (SEQ ID NO:9)

pOKSC41a (212 bp)

GTCTGGAGTT CAAAACCATC CTGGCATTTA TGGT-GAAACC CTGTCTCTAC TAAAAATACA 60 AAATA-GACAG GTGTGGGTGT CACGCCTGTA GTC-CCAGCTA CTCGGAAGGC TGAGGCAGGA 120
GAATCGCTTG AACCTGGGAG GCAGAGGTTG CAT-TGAGGCA AGATCGCACC ACTGTACTCC 180 AGC-CAGGGTG ACAGAGCGGG ACTCTGTCAT TT 212 (SEQ ID NO:10)

pOKSC6f (247 bp)

This clone has identity with human beta globin region on chromosome 11, as having a 61.3% identity in 173 bp overlap.

ATGTTATCCC TTGAATGTAG TGTGTAACAG AGAGAGATGT TTCTTTCTTT CTTTGATTAT 60
CTGAGAAGCT AGGCAGGTGA AAGAACTTTC TTGTCCTCCA TTCAGAAATA ATTTACAGGC 120
AGTTACTTCT AAATATGCAT GCCTGGGCCA AAT-GTGGTGG CTCACACCTG TAATCCCAAC 180
CCTGGGAAGC TGAGGCAGGA GGATTGCTTG CAACCAGCCT GGGTAGACAT AGTGAAACCT 240 GTCTCTC 247 (SEQ ID NO:11)

pOKSC8a (32 bp)

AGCCTGGGCG ACAGAGAGCC AAACGCCGTC TG 32 (SEQ ID NO:12)

In the above sequences and description, bp=base pairs, RPA=RNase Protection Assay and PCR=Polymerase Chain Reaction.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. An isolated nucleic acid molecule comprising at least 30 consecutive nucleotides from SEQ ID NO:3, SEQ ID NO:4, SEQ ID NO:5, or SEQ ID NO:9, or from the complementary strand of any one thereof.

2. A nucleic acid molecule in accordance with claim 1, comprising 30–100 consecutive nucleotides from SEQ ID NO:3, SEQ ID NO:4, SEQ ID NO:5, or SEQ ID NO:9, or from the complementary strand of any one thereof.

3. An isolated nucleic acid molecule comprising at least 30 consecutive nucleotides from SEQ ID NO:3, SEQ ID NO:4, SEQ ID NO:5, or SEQ ID NO:9, or from the complementary strand of any one thereof, and further comprising a detectable label such that said molecule can be used as a detectable probe.

4. An isolated molecule comprising a human cDNA molecule which includes the sequence of SEQ ID NO:3, SEQ ID NO:4, SEQ ID NO:5, SEQ ID NO:6, or SEQ ID NO:9, or the complementary strand of any one thereof.

5. An isolated protein encoded by a human cDNA molecule in accordance with claim 4.

6. A vector comprising a nucleic acid molecule comprising at least 30 consecutive nucleotides from SEQ ID NO:3, SEQ ID NO:4, SEQ ID NO:5, or SEQ ID NO:9, or from the complementary strand of any one thereof.

7. A vector in accordance with claim 6, wherein said nucleic acid molecule comprises 30–100 consecutive nucleotides from SEQ ID NO:3, SEQ ID NO:4, SEQ ID NO:5, or SEQ ID NO:9, or from the complementary strand of any one thereof.

8. A vector comprising a nucleic acid molecule in accordance with claim 4.

9. A host cell comprising a vector in accordance with claim 6.

10. A host cell comprising a vector in accordance with claim 7.

11. A host cell comprising a vector in accordance with claim 8.

12. A nucleic acid molecule in accordance with claim 1, comprising at least 30 consecutive nucleotides from SEQ ID NO:3, or from the complementary strand thereof.

13. A nucleic acid molecule in accordance with claim 12 comprising 30–100 consecutive nucleotides from SEQ ID NO:3, or from the complementary strand thereof.

14. A nucleic acid molecule in accordance with claim 12, further comprising a detectable label such that said molecule can be used as a detectable probe.

15. A molecule in accordance with claim 4 comprising a human cDNA molecule which includes the sequence of SEQ ID NO:3, or the complementary strand thereof.

16. An isolated protein encoded by a human cDNA molecule in accordance with claim 15.

17. A vector comprising a nucleic acid molecule in accordance with claim 12.

18. A vector comprising a nucleic acid molecule in accordance with claim 13.

19. A vector comprising a nucleic acid molecule in accordance with claim 15.

20. A host cell comprising a vector in accordance with claim 17.

21. A host cell comprising a vector in accordance with claim 18.

22. A host cell comprising a vector in accordance with claim 19.

23. An isolated nucleic acid molecule comprising at least 60 consecutive nucleotides from SEQ ID NO:6, or from the complementary strand thereof, and further comprising a detectable label such that said molecule can be used as a detectable probe.

24. A vector comprising a nucleic acid molecule comprising at least 60 consecutive nucleotides from SEQ ID NO:6, or from the complementary strand thereof.

25. A vector comprising a nucleic acid molecule comprising 60–100 consecutive nucleotides from SEQ ID NO:6, or from the complementary strand thereof.

26. A host cell comprising the vector in accordance with claim 24.

27. A host cell comprising the vector in accordance with claim 25.

* * * * *